United States Patent [19]
Shuber

[11] Patent Number: 5,834,181
[45] Date of Patent: *Nov. 10, 1998

[54] HIGH THROUGHPUT SCREENING METHOD FOR SEQUENCES OR GENETIC ALTERATIONS IN NUCLEIC ACIDS

[75] Inventor: Anthony P. Shuber, Milford, Mass.

[73] Assignee: Genzyme Corporation, Framingham, Mass.

[ * ] Notice: The term of this patent shall not extend beyond the expiration date of Pat. No. 5,589,330.

[21] Appl. No.: 710,134

[22] Filed: Sep. 13, 1996

Related U.S. Application Data

Related U.S. Application Data

[60] Provisional application No. 60/003,788, Sep. 15, 1995.

[63] Continuation-in-part of Ser. No. 281,940, Jul. 28, 1994, Pat. No. 5,589,330, and a continuation-in-part of Ser. No. 485,885, Jun. 7, 1995.

[51] Int. Cl.$^6$ .............. C12Q 1/70; C12Q 1/68; C12P 19/34
[52] U.S. Cl. ............... 435/5; 435/6; 435/91.1; 435/91.2
[58] Field of Search ................ 435/5, 6, 91.1, 435/91.2; 935/78

[56] References Cited

U.S. PATENT DOCUMENTS

| | | | |
|---|---|---|---|
| 4,824,776 | 4/1989 | Heller | 435/6 |
| 5,217,863 | 6/1993 | Cotton et al. | 435/6 |
| 5,348,855 | 9/1994 | Dattagupta et al. | 435/6 |
| 5,382,510 | 1/1995 | Levine et al. | 435/6 |
| 5,387,510 | 2/1995 | Wu | 435/91.2 |
| 5,401,630 | 3/1995 | Török et al. | 435/6 |
| 5,434,049 | 7/1995 | Okano et al. | 435/6 |
| 5,459,039 | 10/1995 | Modrich et al. | 435/6 |
| 5,470,705 | 11/1995 | Grossman et al. | 435/6 |
| 5,514,543 | 5/1996 | Grossman et al. | 435/6 |

FOREIGN PATENT DOCUMENTS

| | | |
|---|---|---|
| 582256A2 | 2/1994 | European Pat. Off. . |
| WO93/02216 | 2/1993 | WIPO . |

OTHER PUBLICATIONS

Carlsson et al., (1996), *Nature* 380:207.
Chehab et al., (1987), *Nature* 329: 293–294.
Chetverin et al., (1994), *Bio/Technology* 12: 1093–1099.
Drmanac, R.T., Biochip Array Technologies—Fabrications & Applications, May 10, 1995 (Abstract).

(List continued on next page.)

*Primary Examiner*—Kenneth R. Horlick

[57] ABSTRACT

The present invention provides methods for identifying genetic alterations in a target sequence present in a nucleic acid sample, comprising immobilizing samples on a support, contacting the samples simultaneously with different purine and pyrimidine containing polymers under conditions of hybridization, separating the hybridized polymers from the samples; and identifying the hybridized polymers to identify the genetic alteration(s). The present invention also provides methods for identifying target sequences present in a nucleic acid sample, comprising immobilizing nucleic acid samples on a support, contacting the samples simultaneously different purine and pyrimidine containing polymers under hybridization conditions, separating the polymers from the complementary target sequence(s), and identifying the hybridized polymers to identify the target sequence(s). Further provided by the present invention are methods for identifying randomly permuted genetic alterations in a target sequence present in a nucleic acid sample, comprising immobilizing nucleic acid samples on a support, contacting the samples simultaneously with different purine and pyrimidine containing polymers under hybridization conditions, detecting hybridization between the polymers and the complementary target sequences, to identify the target sequence(s), separating the hybridized polymers from the complementary target sequences; and identifying randomly permuted genetic alterations present in the target sequence.

18 Claims, 14 Drawing Sheets

OTHER PUBLICATIONS

Forrest et al., (1995) *Nature Genetics* 10:375–376.
Grompe et al., *Nature Genetics* 5:111–117.
Haliassos et al., (1989), *Nucleic Acids Research* 17:3606.
Hajra et al., (1992), *Pharmacogenetics* 2:78–88.
Maxam A.M., (1977), *Proc. Natl. Acad. Sci., USA* 74(2):560–564.
Mayall et al., (1990) *J. Med. Genet.* 27:658.
Mirzabekov, A.D., (1994), *Tr. Biotch.* 12:27–32.
Pease et al., *Proc. Natl. Acad. Sci., USA* 980:5022–5026.
Richards et al., (1993), *Human Mol. Genetics.* 2(2):560–564.
Rommens et al., (1980), *AM.J. Hum. Genet.* 46:395–396.
Saiki et al., (1986), *Nature* 324:163–166.
Saiki et al., (1988), *Science* 239:487–491.
Sanger et al., (1977), *Proc. Natl. Acad. Sci. USA,* 74:5463.
Shuber et al., (1993), *Human Molecular Genetics* 2(2):153–158.
Shuber et al., (1995), *Genome Research* 5:488–493.
Southern, E.M., (1975), *J. Mol. Biol.* 98:503–517.
Southern, E.M., (1996), *Tr. Genetics* 12(3):110–115.
Wood et al., (1985), *Proc. Natl. Acad. Sci., USA* 82:1585.
Wyman et al., (1980), *Proc. Natl. Acad. Sci. USA* 77:6754–6758.

Phase I Results

Dot Blot Results Generated from Combinatorial Hybridization

A panel of different patient samples hybridized with pools of mutation specific oligonucelotides

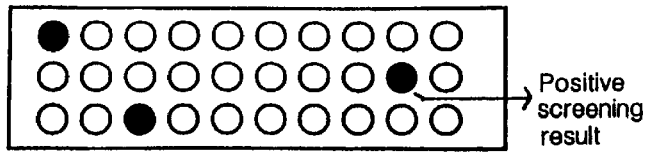

Positive screening result

↓ Identification of specific mutations

Positives Punched Out and Placed into Epp. Tubes (30 min.) 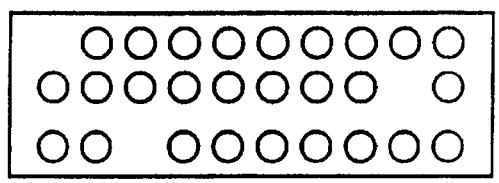 → 

↓

Oligos Eluted Off of Solid Support (15 min.) 

↓

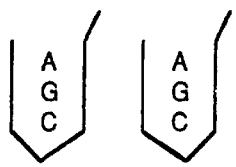  —Maxim Glibert (2-3 hrs)
—Sanger (30 min)
—Amplification/Sanger

Chemical or Enzymatic Sequencing Reactions

↓

Reactions Loaded onto Automated Sequencer

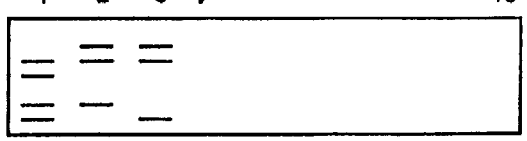

Sample Capacity= ~240 samples/hr

↓

Software Analysis    Mutation Results
(Next Day)

FIG. 4

Model 1
(chemical Cleavage)
Solid Phase Capture of Ligation products from positive reaction
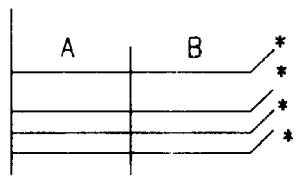
Chemical Cleavage Reaction
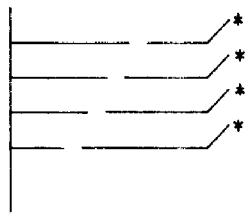
Run Seqencing Gel
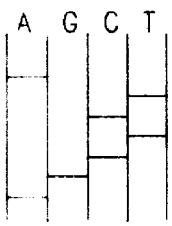
Software Analysis and Mutation Identification
FIG. 6

Model 2
(Ligation Product Used as Primer in Sanger Seq.Reaction)
Solid Phase Capture of Ligation products from positive reaction
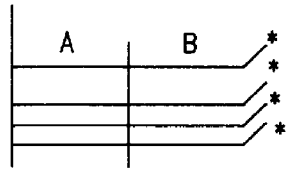
Add Heterogeneous Population of Target Seqs. and Perform Sanger Seq. reaction in the presence of labeled ddNTP.
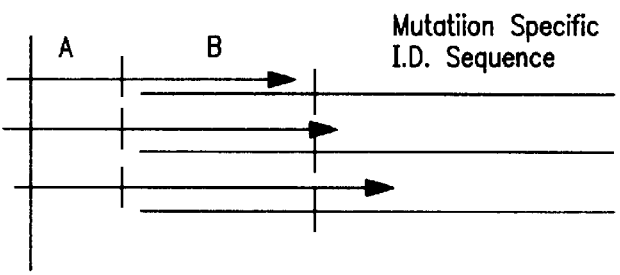
Cleave Sequencing Products Off of Solid Support and Run Gel
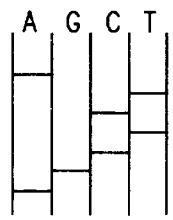
Software Analysis and Mutation Identification
FIG. 7

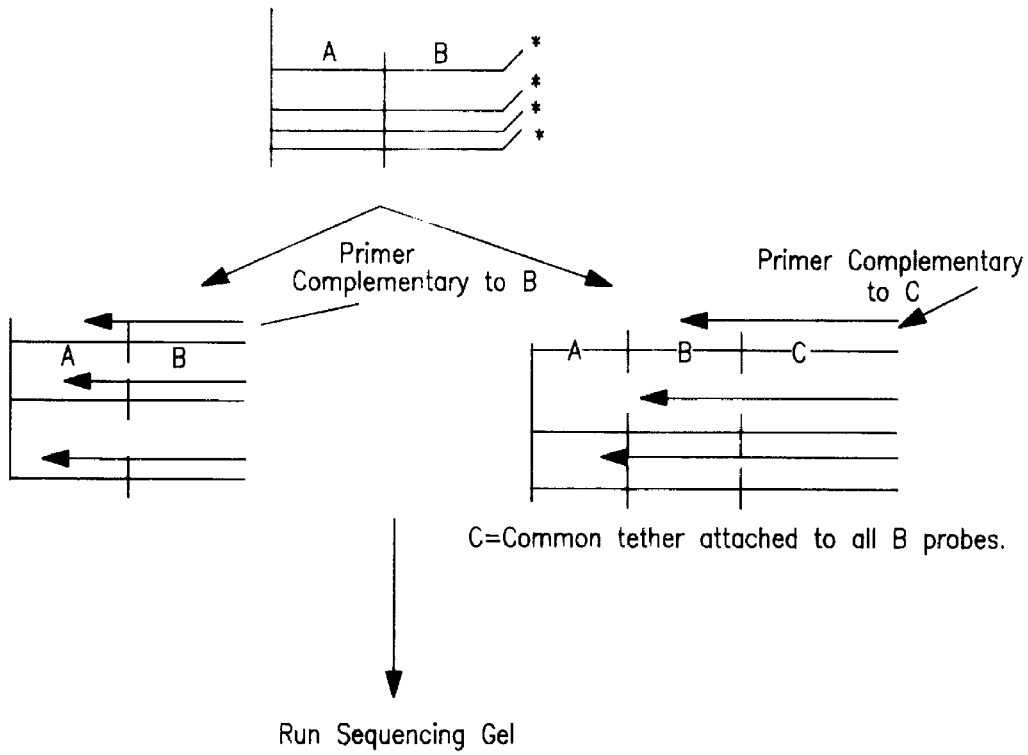

Model 3
(Ligation product(s) directly sequenced with heterogeneous primers complementary to all B sequences used in the ligation or with a primer complementary to a common 3' tether added to all B probes)

Solid Phase Capture of ligation products from positive reaction

Primer Complementary to B

Primer Complementary to C

C=Common tether attached to all B probes.

Run Sequencing Gel

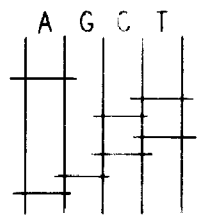

Software Analysis and Mutation Identification

FIG. 8

Model 4
(Utilize ligation product as primer for amplification and sequence product)
Solid Phase Capture of ligation products from positive reaction (or) Perform in-solution
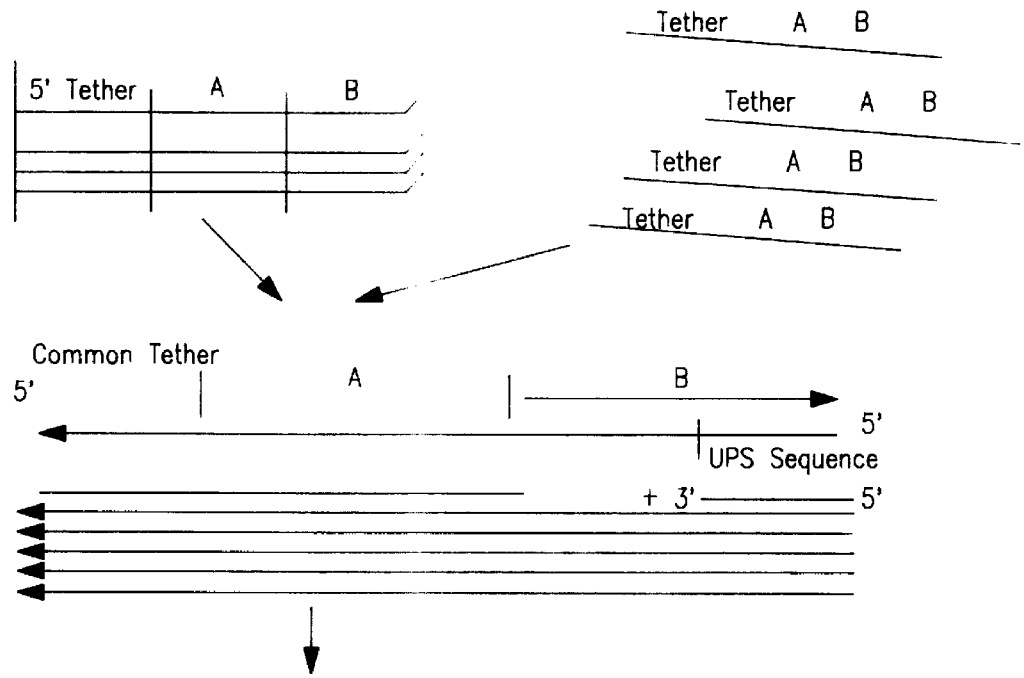
Sequence linear amplification products with primer complementary to tether sequence
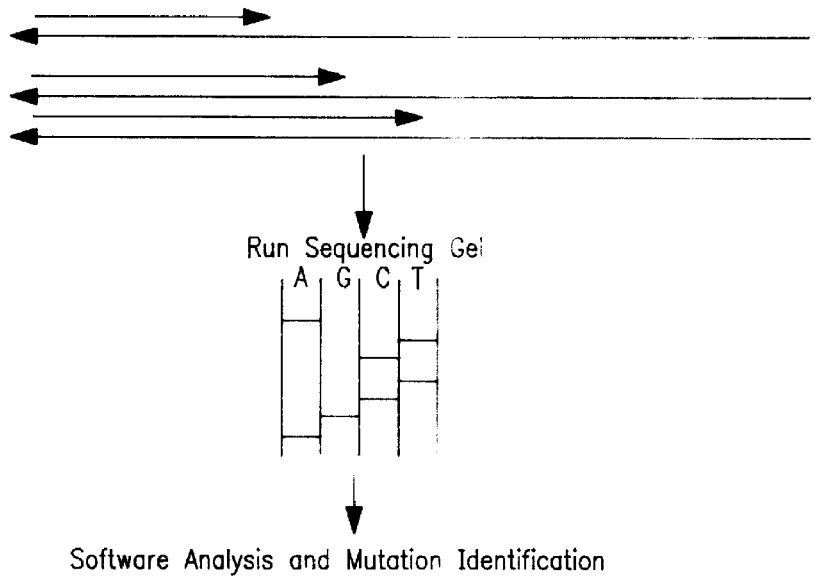
Software Analysis and Mutation Identification
FIG. 9

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:1:

ACACCAATGA TATTTTC 17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:2:

ATTCCACCTT CTCAAAG 17

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:3:

CTCGTTGATC TCCACTC 17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:4:

CTCATTGACC TCCACTC 17

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:5:

CTTTCCTTCA CTGTTGC 17

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:6:

TCATAGGGAT CCAACTT                                                                              17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:7:

ACACCAAAGA TATTTTC                                                                              17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:8:

CGATAGAGTG TTCCTCC                                                                              17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:9:

GCAAGGAAGT ATTAACT                                                                              17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:10:

CTCGTTGACC TCCATTC                                                                              17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:11:

TATTCACGTT GCTAAAG  17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:12:

GGAGATGTCT TATTACC  17

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:13:

ACTCACCATT TTAATAC  17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:14:

GTAGTCTCAA AAAAAGC  17

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:15:

GTGACCGCCA TGGGCAG  17

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

-continued ( x i ) SEQUENCE DESCRIPTION: SEQ ID NO:16:

CACCACAAGA ACCCTGA												17

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:17:

GGAATATTCA CTTTCCA												17

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:18:

GCAGTGTTCA AATCCCA												17

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:19:

CATAATTCAT CAAATTT												17

( 2 ) INFORMATION FOR SEQ ID NO:20:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:20:

CTCAGCTCAC AGATCGC												17

( 2 ) INFORMATION FOR SEQ ID NO:21:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:21:

CATATCTTTC AAATATT 17

( 2 ) INFORMATION FOR SEQ ID NO:22:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:22:

CTTGTAGGTT TACCTTC 17

( 2 ) INFORMATION FOR SEQ ID NO:23:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:23:

GATTTCATAG AACATAA 17

( 2 ) INFORMATION FOR SEQ ID NO:24:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:24:

GATTGCTTTT TGTTTCT 17

( 2 ) INFORMATION FOR SEQ ID NO:25:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:25:

AACCTCCAAC AACTGTC 17

( 2 ) INFORMATION FOR SEQ ID NO:26:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:26:

TTCCAGAGGA TGATTCC 17

( 2 ) INFORMATION FOR SEQ ID NO:27:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:27:

AGTTAAATCG CGATAGA 17

( 2 ) INFORMATION FOR SEQ ID NO:28:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:28:

TCCCCTCAGT GTGATTC 17

( 2 ) INFORMATION FOR SEQ ID NO:29:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:29:

ACTAAGAACA GAATGAA 17

( 2 ) INFORMATION FOR SEQ ID NO:30:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:30:

GATGAAGCTT CTGTATC 17

( 2 ) INFORMATION FOR SEQ ID NO:31:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

(x i) SEQUENCE DESCRIPTION: SEQ ID NO:31:

ACAGTTACAA GAACCAG 17

(2) INFORMATION FOR SEQ ID NO:32:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

(x i) SEQUENCE DESCRIPTION: SEQ ID NO:32:

GTGACCGCCA TGTGCAG 17

(2) INFORMATION FOR SEQ ID NO:33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

(x i) SEQUENCE DESCRIPTION: SEQ ID NO:33:

CATAGGAAAC ACCAAAG 17

(2) INFORMATION FOR SEQ ID NO:34:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

(x i) SEQUENCE DESCRIPTION: SEQ ID NO:34:

ATTCCACCTT CTCCAAG 17

(2) INFORMATION FOR SEQ ID NO:35:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

(x i) SEQUENCE DESCRIPTION: SEQ ID NO:35:

CTCGTTGACC TCCACTC 17

(2) INFORMATION FOR SEQ ID NO:36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

(x i) SEQUENCE DESCRIPTION: SEQ ID NO:36:

CTTTCCTCCA CTGTTGC 17

(2) INFORMATION FOR SEQ ID NO:37:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

(x i) SEQUENCE DESCRIPTION: SEQ ID NO:37:

TCATAGGGAT CCAAGTT 17

(2) INFORMATION FOR SEQ ID NO:38:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

(x i) SEQUENCE DESCRIPTION: SEQ ID NO:38:

ACACCAAAGA TGATATR 17

(2) INFORMATION FOR SEQ ID NO:39:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

(x i) SEQUENCE DESCRIPTION: SEQ ID NO:39:

CGATAGAGCG TTCCTCC 17

(2) INFORMATION FOR SEQ ID NO:40:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

(x i) SEQUENCE DESCRIPTION: SEQ ID NO:40:

GCAAGGAAGT ATTACCT 17

(2) INFORMATION FOR SEQ ID NO:41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Oligonucleotides"

( x i ) SEQUENCE DESCRIPTION: SEQ ID NO:41:

TATTCACCTT GCTAAAG 17

( 2 ) INFORMATION FOR SEQ ID NO:42:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:42:

GGAGATGTCC TATTACC 17

( 2 ) INFORMATION FOR SEQ ID NO:43:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:43:

ACTCGCCATT TTAATAC 17

( 2 ) INFORMATION FOR SEQ ID NO:44:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:44:

GTAGTCTCAA AAAAGCT 17

( 2 ) INFORMATION FOR SEQ ID NO:45:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:45:

GTGACCGCCA TGCGCAG 17

( 2 ) INFORMATION FOR SEQ ID NO:46:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:46:

CACCACAAAG AACCCRG 17

( 2 ) INFORMATION FOR SEQ ID NO:47:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:47:

GGAATACTCA CTTTCCA 17

( 2 ) INFORMATION FOR SEQ ID NO:48:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:48:

GCAGTGTTCA AATCTCA 17

( 2 ) INFORMATION FOR SEQ ID NO:49:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:49:

CATACTTCAT CAAATTT 17

( 2 ) INFORMATION FOR SEQ ID NO:50:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:50:

CTCGGCTCAC AGATCGC 17

( 2 ) INFORMATION FOR SEQ ID NO:51:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:51:

CATACCTTTC AAATATT　　　　　　　　　　　　　　　　　　　　　　　　　　　17

( 2 ) INFORMATION FOR SEQ ID NO:52:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:52:

CTTGGTAGGT TTACCTT　　　　　　　　　　　　　　　　　　　　　　　　　　　17

( 2 ) INFORMATION FOR SEQ ID NO:53:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:53:

GATTCCATAG AACATAA　　　　　　　　　　　　　　　　　　　　　　　　　　　17

( 2 ) INFORMATION FOR SEQ ID NO:54:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:54:

GATTGTTTTT TTGTTTC　　　　　　　　　　　　　　　　　　　　　　　　　　　17

( 2 ) INFORMATION FOR SEQ ID NO:55:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( x i ) SEQUENCE DESCRIPTION: SEQ ID NO:55:

AACCGCCAAC AACTGTC　　　　　　　　　　　　　　　　　　　　　　　　　　　17

( 2 ) INFORMATION FOR SEQ ID NO:56:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

-continued (xi) SEQUENCE DESCRIPTION: SEQ ID NO:56:

TTCCGGAGGA TGATTCC　　　　　　　　　　　　　　　　　　　　　17

(2) INFORMATION FOR SEQ ID NO:57:

(i) SEQUENCE CHARACTERISTICS:
　　　　(A) LENGTH: 17 base pairs
　　　　(B) TYPE: nucleic acid
　　　　(C) STRANDEDNESS: single
　　　　(D) TOPOLOGY: linear (ii) MOLECULE TYPE: other nucleic acid
　　　　(A) DESCRIPTION: /desc = "Oligonucleotides"

(xi) SEQUENCE DESCRIPTION: SEQ ID NO:57:

AGATAAATCG CGATAGA　　　　　　　　　　　　　　　　　　　　　17

(2) INFORMATION FOR SEQ ID NO:58:

(i) SEQUENCE CHARACTERISTICS:
　　　　(A) LENGTH: 17 base pairs
　　　　(B) TYPE: nucleic acid
　　　　(C) STRANDEDNESS: single
　　　　(D) TOPOLOGY: linear (ii) MOLECULE TYPE: other nucleic acid
　　　　(A) DESCRIPTION: /desc = "Oligonucleotides"

(xi) SEQUENCE DESCRIPTION: SEQ ID NO:58:

TCCACTCAGT GTGATTC　　　　　　　　　　　　　　　　　　　　　17

(2) INFORMATION FOR SEQ ID NO:59:

(i) SEQUENCE CHARACTERISTICS:
　　　　(A) LENGTH: 17 base pairs
　　　　(B) TYPE: nucleic acid
　　　　(C) STRANDEDNESS: single
　　　　(D) TOPOLOGY: linear (ii) MOLECULE TYPE: other nucleic acid
　　　　(A) DESCRIPTION: /desc = "Oligonucleotides"

(xi) SEQUENCE DESCRIPTION: SEQ ID NO:59:

ACTGAGAACA GAATGAA　　　　　　　　　　　　　　　　　　　　　17

(2) INFORMATION FOR SEQ ID NO:60:

(i) SEQUENCE CHARACTERISTICS:
　　　　(A) LENGTH: 17 base pairs
　　　　(B) TYPE: nucleic acid
　　　　(C) STRANDEDNESS: single
　　　　(D) TOPOLOGY: linear (ii) MOLECULE TYPE: other nucleic acid
　　　　(A) DESCRIPTION: /desc = "Oligonucleotides"

(xi) SEQUENCE DESCRIPTION: SEQ ID NO:60:

GATGACGCTT CTGTATC　　　　　　　　　　　　　　　　　　　　　17

(2) INFORMATION FOR SEQ ID NO:61:

(i) SEQUENCE CHARACTERISTICS:
　　　　(A) LENGTH: 17 base pairs
　　　　(B) TYPE: nucleic acid
　　　　(C) STRANDEDNESS: single
　　　　(D) TOPOLOGY: linear (ii) MOLECULE TYPE: other nucleic acid
　　　　(A) DESCRIPTION: /desc = "Oligonucleotides"

-continued ( x i ) SEQUENCE DESCRIPTION: SEQ ID NO:61:

ACAGGTACAA GAACCAG　　　　　　　　　　　　　　　　　　　　　　　　　　　　　　　　17

( 2 ) INFORMATION FOR SEQ ID NO:62:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Oligonucleotides"

( x i ) SEQUENCE DESCRIPTION: SEQ ID NO:62:

AAGGTCTCCT ACTAAGGTCT CGCTTCGTTT CATCTCATCT CG　　　　　　　　　　　　　　　42

( 2 ) INFORMATION FOR SEQ ID NO:63:

( i ) SEQUENCE CHARACTERISTICS:
  ( A ) LENGTH: 66 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Oligonucleotides"

( x i ) SEQUENCE DESCRIPTION: SEQ ID NO:63:

AAGGTCTCCT ACTAAGGTCT CGCTTGCTTT CATCTCATCT CGATCGATCG ATCGATCGAT　　　　60

CGATCG　　　　　　　　　　　　　　　　　　　　　　　　　　　　　　　　　　　　　　66

( 2 ) INFORMATION FOR SEQ ID NO:64:

( i ) SEQUENCE CHARACTERISTICS:
  ( A ) LENGTH: 86 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Oligonucleotides"

( x i ) SEQUENCE DESCRIPTION: SEQ ID NO:64:

AAGGTCTCCT ACTAAGGCGC CAGGGTTTTC CCAGTCATCT CGCTTCGTTC ATCTCATCTC　　　　60

GATCGATCGA TCGATCGATC GATCGA　　　　　　　　　　　　　　　　　　　　　　　　　86

( 2 ) INFORMATION FOR SEQ ID NO:65:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Oligonucleotides"

( x i ) SEQUENCE DESCRIPTION: SEQ ID NO:65:

TTCCAGAGGA TGATTCC　　　　　　　　　　　　　　　　　　　　　　　　　　　　　　　17

HIGH THROUGHPUT SCREENING METHOD FOR SEQUENCES OR GENETIC ALTERATIONS IN NUCLEIC ACIDS

This application is a Continuation-in-part of application Ser. No. 08/281,940 filed Jul. 28, 1994 U.S. Pat. No. 5,589,330, and of Ser. No. 08/485,885 filed Jun. 7, 1995, and of provisional Ser. No. 60/003,788, filed Sep. 15, 1995 the entire contents of which are hereby incorporated by reference herein.

FIELD OF THE INVENTION

This invention pertains to high throughput screening of nucleic acid samples in order to identify the presence of one or more genetic alterations of interest in those samples. This invention also pertains to the identification of specific target nucleic acid sequences associated with genetic disorders. The methods of the present invention can be used to identify genetic polymorphisms, to determine the molecular basis for genetic diseases, and to provide carrier and prenatal diagnosis for genetic counseling. Furthermore, the invention pertains to specific high-resolution identification of disease-causing microorganisms.

BACKGROUND OF THE INVENTION

Over the last several years, there has been a significant increase in the number of identified, cloned, and characterized genes found to be responsible for inherited diseases in humans. As the number of disease-associated sequences have increased, so has the number of mutations identified within the genes. In some genes, only one or a few mutations are specifically responsible for the disease phenotype (e.g. sickle cell anemia ) (1). However, in most disease genes, many different causative mutations exist with no one mutation present at a significant frequency within an affected patient population. Therefore, for both research and clinical diagnostic applications, improved methods of mutation analysis are required not only to confirm that a candidate gene truly represents the disease gene, but also to build mutation databases and provide clinical diagnostic assays. In addition, with the increasing number of cancer genes being discovered (2–4), efficient, cost effective, and highly informative mutation analysis procedures are necessary in order to better understand predisposition and polygenic diseases.

This has led to the development of two broad categories of mutation detection technologies (5,6). The first group, designed to scan for mutations within a gene, includes single-strand conformational polymorphism (SSCP) (7), denaturing gradient-gel electrophoresis (DGGE) (8), heteroduplex analysis (HET) (9), chemical cleavage analysis (CCM) (10), ribonuclease cleavage (RNAase) (11), and direct sequencing of the target (12). Although these procedures are highly informative, they can be tedious and are incompatible with high throughput and low cost. Given the need in the clinical diagnostic laboratory to be able to analyze large numbers of samples (>500 samples/analysis) cost effectively, these scanning procedures are not currently used as routine methods of mutation detection (5).

In the second group, more direct methods of mutation analysis have been developed such as allele-specific amplification (ASA) (13), oligonucleotide ligation assay (OLA) (14), primer extension (15), artificial introduction of restriction sites (AIRS) (16), allele-specific oligonucleotide hybridization (ASO) (17), and variations of these procedures. Together with robotics, these methods for direct mutation analysis have helped in reducing cost and increasing throughput when only a limited number of mutations need to be analyzed for efficient diagnostic purposes. However, given that many of the mutations identified in disease genes are rare, for most populations undergoing testing, large numbers of mutations must be analyzed in order to achieve significant detection frequencies.

Many methods have been developed for the detection of known mutations. In general, these diagnostic technologies have been designed to be simple and cost effective. However, a significant limitation in almost all of the currently available techniques is the inability to analyze a large number of samples simultaneously for a large number of mutations. The most applicable format for the analysis of large numbers of samples is the dot blot, wherein the PCR products are bound to a filter membrane and hybridized with allele-specific probes. However, in a standard forward dot blot procedure a separate hybridization is performed for each allele or mutation of interest. Therefore, if the number of probes is large, this procedure becomes cumbersome.

Unfortunately comprehensive multiplex mutation analysis, for example, >100 mutations, cannot readily be performed by any currently available diagnostic method while retaining the sample throughput and cost effectiveness needed in a clinical diagnostic laboratory. Therefore, a significant effort is needed in order to develop a procedure that will allow large numbers of samples to be analyzed in a single assay.

SUMMARY OF THE INVENTION

The present invention encompasses high-throughput methods for detecting and identifying sequences or genetic alterations (defined as nucleotide additions, deletions, or substitutions) in a large number of nucleic acid samples, which is achieved by: immobilizing a plurality of the nucleic acid samples on a support; providing a multiplicity of purine and pyrimidine containing polymers; hybridizing the immobilized samples with the multiplicity of purine and pyrimidine containing polymers at substantially the same time; identifying the hybridized purine and pyrimidine containing polymers wherein the identification of the hybridized purine and pyrimidine containing polymers identifies the nucleic acid sequence or one or more genetic alterations. The hybridized purine and pyrimidine polymers can be identified by any method well-known in the art, such as, for example, sequencing, direct labeling, indirect labeling, and labeling with a unique length marker.

The present invention also encompasses certain embodiments wherein the sample is not immobilized, and is reacted with the purine and pyrimidine containing polymers in solution (i.e., rather than on a support).

Both the target nucleic acid sequence and/or the hybridized purine and pyrimidine containing polymers may be amplified to facilitate detection and identification. Non-limiting examples of amplification methods include polymerase chain reaction (PCR), ligase chain reaction (LCR), gap-LCR, ligation amplification reaction (LAR), oligonucleotide ligation assay (OLA), amplification refractory mutation system (ARMS), competitive oligonucleotide priming (COP), allele specific PCR, Q-beta replicase amplification, nucleic acid sequence based amplification (NASBA) and branched chain amplification. Hybridizations can be carried out under conditions that minimize the differences in melting temperature of hybrids formed between different purine and pyrimidine containing polymers and the target nucleic acid sequence.

BRIEF DESCRIPTION OF THE DRAWINGS

FIG. 4 shows a schematic representation of the methods of the present invention.

FIG. 6 depicts a scheme for identifying ligation products through chemical cleavage sequencing of the products, i.e., Maxam-Gilbert sequencing.

FIG. 7 depicts a scheme for identifying ligation products using a conventional Sanger type sequencing reaction.

FIG. 8 depicts another method for identifying ligation products by Sanger sequencing.

FIG. 9 depicts Sanger sequencing of ligation products that are amplified using a universal priming sequence.

DETAILED DESCRIPTION OF THE INVENTION

Figure 1:
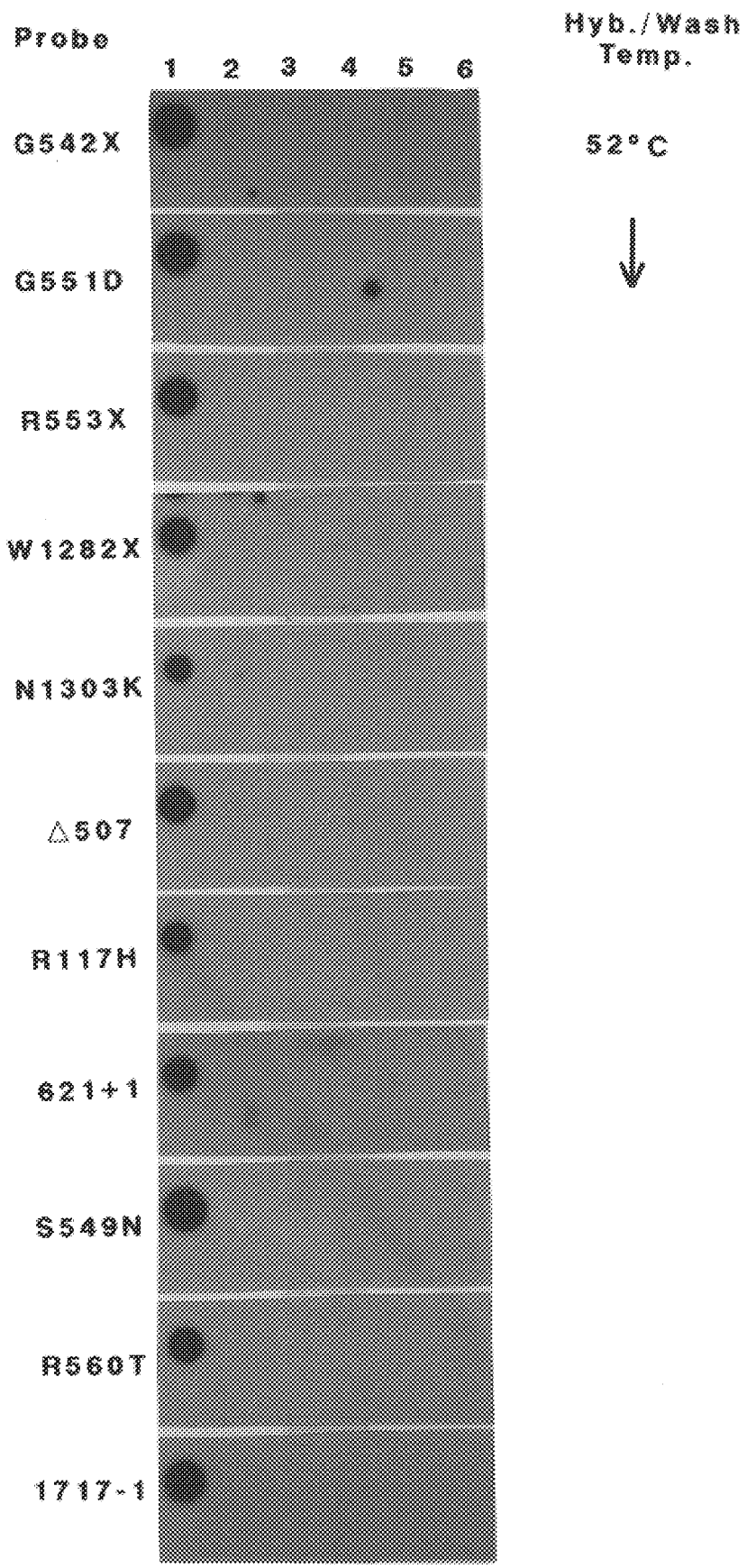
FIG. 1 shows autoradiographic results obtained from hybridizing multiple identical filters containing human genomic DNA with $^{32}$P-labelled ASOs specific for different alleles of the cystic fibrosis transmembrane regulator (CFTR) gene. The ASOs used in each hybridization are identified on the left of each filter. Lane 1 in each case contains DNA carrying the mutant sequence complementary to each ASO; lanes 2–6 contain wild-type "normal" sequences.
Figure 2A:
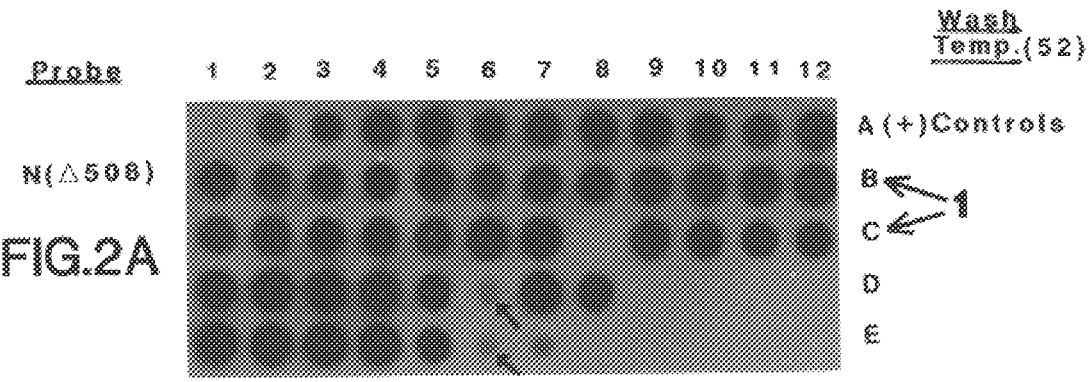
FIGS. 2A–2D show autoradiographic results obtained from hybridizing four identical filters containing human genomic DNA with $^{32}$P-labelled ASOs specific for different alleles of the cystic fibrosis transmembrane regulator (CFTR) gene. The ASOs used in each hybridization are identified on the left of each filter. The lanes marked A contain positive control DNA samples. Rows B–E contain patient samples analyzed in duplicate, with the exception of 8C (amplification failure on duplicate sample), and D7, D8 and E7 (positive controls).
Figure 2B:
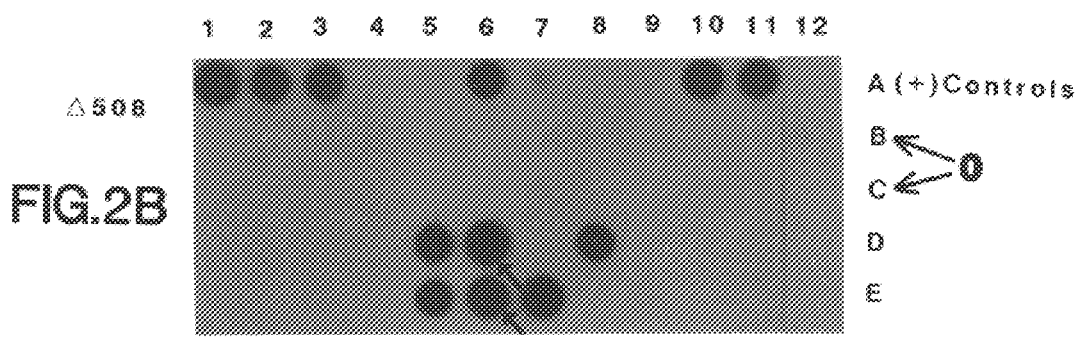
Figure 2C:
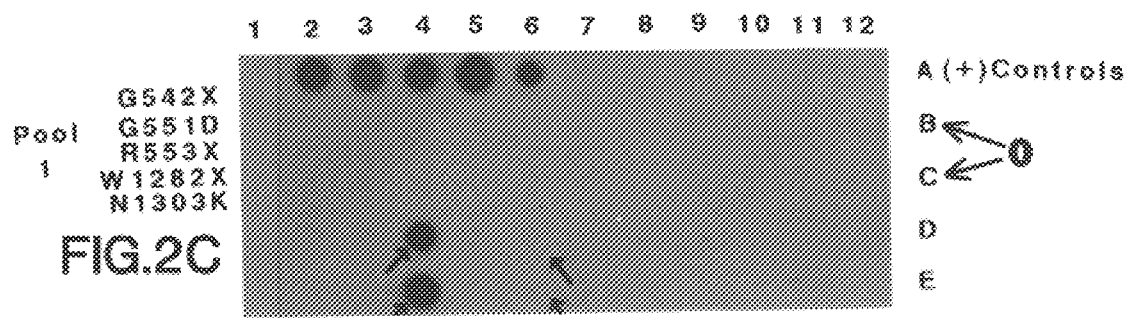
Figure 2D:
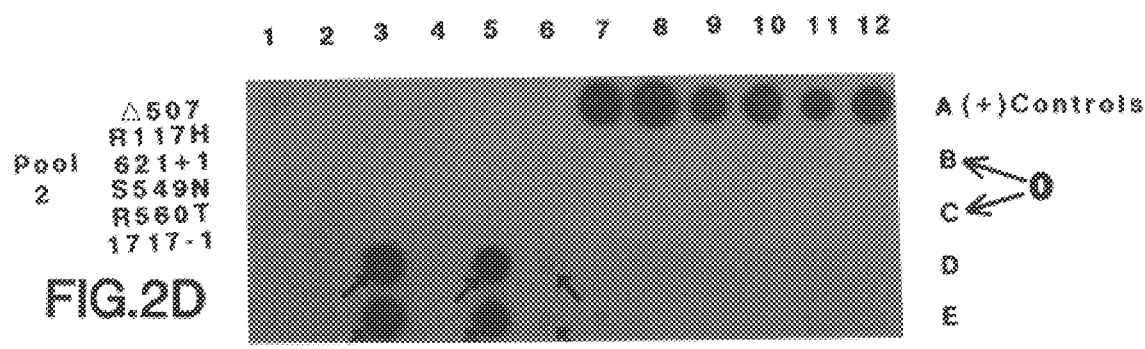

All patent applications, patents, and literature references cited in this specification are hereby incorporated by reference in their entirety. In case of conflict, the present description, including definitions, will control.

Definitions

1. An "allele-specific oligonucleotide" (ASO) as defined herein is an oligonucleotide having a sequence that is identical or almost identical to a known nucleic acid portion. Often, an ASO contains a small change relative to the prevalent "wild type" sequence. This change may comprise addition, deletion, or substitution of one or more nucleotides. ASOs can be designed to identify any addition, deletion, or substitution, as long as the nucleic acid sequence is known.

2. A "variant" sequence as used herein encompasses a nucleic acid sequence that differs from a known sequence by the addition, deletion, or substitution of one or more nucleotides.

3. "Amplification" of a nucleic acid sequence as used herein denotes the use of polymerase chain reaction (PCR) (Saiki et al., Science 239:487, 1988), ligase chain reaction (Barany, Proc. Natl. Acad. Sci. U.S.A. 83:139, 1991) (LCR), gap-LCR (Abravaya et al., Nuc. Acids Res. 23:675, 1995), ligation amplification reaction (Wu et al., Genomics 4:560, 1989); ASPCR (Wu et al., Proc. Natl. Acad. Sci. U.S.A. 86:2757, 1989), ARMS (Newton et al., Nucl. Acids Res. 17:2503, 1989), or other methods to increase the concentration of a particular nucleic acid sequence.

4. "Chemical sequencing" of nucleic acids denotes methods such as that of Maxim and Gilbert (Maxim-Gilbert sequencing, Maxam and Gilbert, 1977, Proc. Natl. Acad. Sci. U.S.A. 74:560), in which nucleic acids are randomly cleaved using individual base-specific reactions.

5. "Enzymatic sequencing" of nucleic acid denotes methods such as that of Sanger (Sanger et al., 1977, Proc. Natl. Acad. Sci. U.S.A., 74:5463), in which a single-stranded DNA is copied and randomly terminated using DNA polymerase.

6. In this specification, the terms "bound" and "hybridized" are used interchangeably to denote the formation of nucleic acid:purine and pyrimidine containing polymer duplexes. The term "affinity purified" denotes purification using hybridization.

7. "High-throughput" denotes the ability to simultaneously process and screen a large number of nucleic acid samples (e.g., in excess of 50 or 100 nucleic acid samples) and a large number of target sequences within those samples.

8. "Purine and pyrimidine containing polymers" is mean: to include DNA, RNA and other polymers containing purines and pyrimidines that are capable of Watson-Crick base pairing, and which do no: necessarily carry a sugar phosphate backbone, such as PNA. See, J. Am. Chem. Soc., 114:1895–97 (1992).

The present invention provides refinements of a modified allele-specific oligonucleotide approach for the simultaneous analysis of large numbers of patient samples for multiple CF mutations (25). Invention methods further provide a Multiplex Allele-Specific Diagnostic Assay (MASDA), which has the capacity to cost effectively analyze large numbers of samples (>500) for a large number of mutations (>100) in a single assay. Like the more familiar 'chip' technologies (19–22), MASDA uses oligonucleotide hybridization to interrogate DNA sequences. However, in contrast to many oligonucleotide array approaches, in the invention MASDA technology, the target DNA is immobilized to the solid support, and interrogated in a combinatorial fashion with a pool of ASOs (i.e. a single mixture of mutation-specific oligonucleotides) in solution. By retaining the forward dot blot format, it is possible to simultaneously analyze large numbers of samples (>500) for a large number of mutations (>100). In phase I of the combinatorial analysis, the ASO(s) corresponding to the specific mutation (s) present in a given sample is hybrid-selected from the pool by the target DNA. Following removal of unhybridized ASOs, sequence-specific band patterns associated with the bound ASOs are generated by chemical or enzymatic sequencing, and the mutation or mutations present in the sample are easily identified. Using the gene targets CFTR (26), β-globin (1), HEXA (27), GCR (28), ASPA (29), BRCA1 (3), and FACC (30) as a model system, we demonstrate that MASDA not only allows different patient samples with different disease indications to be analyzed in a single assay, but allows the identification of multiple mutations within a single gene or multiple genes in a single patient's DNA sample.

The present invention encompasses a high-throughput method for screening nucleic acid samples for target sequences or sequence alterations and, more particularly, for specific DNA sequences in DNA isolated from a patient. The method is applicable when one or more genes or genetic loci are targets of interest. It will also be appreciated that this method allows for rapid and economical screening of a large number of nucleic acid samples for target sequences of interest.

In one embodiment, the specific nucleic acid sequence comprises a portion of a nucleic acid, a particular gene, or a genetic locus in a genomic DNA known to be involved in a pathological condition or syndrome. Non-limiting examples include cystic fibrosis, sickle-cell anemia, β-thalassemia, and Gaucher's disease.

In another embodiment, the specific nucleic acid sequence comprises part of a particular gene or genetic locus that may not be known to be linked to a particular disease, but in which polymorphism is known or suspected.

In yet another embodiment, the specific nucleic acid sequence comprises part of a foreign genetic sequence e.g. the genome of an invading microorganism. Non-limiting examples include bacteria and their phages, viruses, fungi, protozoa, and the like. The present methods are particularly applicable when it is desired to distinguish between different variants or strains of a microorganism in order to choose appropriate therapeutic interventions.

In accordance with the present invention, the target nucleic acid represents a sample of nucleic acid isolated from a patient. This nucleic acid may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids can include blood, urine, cerebrospinal fluid, semen, and tissue exudates at the site of infection or inflammation. Nucleic acids can be extracted from the cell source or body fluid using any of the numerous methods that are standard in the art. It will be understood that the particular method used to extract the nucleic acid will depend on the nature of the source. The minimum amount of DNA, for example, that can be extracted for use in a preferred form of the present invention is about 5 pg (corresponding to about 1 cell equivalent of a genome size of $4 \times 10^9$ base pairs).

Once extracted, the target nucleic acid may be employed in the present invention without further manipulation. Alternatively, one or more specific regions present in the target nucleic acid may be amplified by PCR. In this case, the amplified regions are specified by the choice of particular flanking sequences for use as primers. Amplification at this step provides the advantage of increasing the concentration of specific nucleic acid sequences within the target sequence population. The length of nucleic acid sequence that can be amplified ranges from 80 bp to up to 30 kbp (Saiki et al., 1988, Science, 239:487)

In one embodiment, the target nucleic acid, with or without prior amplification of particular sequences, is bound to a solid phase or semi-solid phase matrix. This allows for the simultaneous processing and screening of a large number of nucleic acid samples from different sources. Non-limiting examples of matrices suitable for use in the present invention include nitrocellulose or nylon filters, glass beads, magnetic beads coated with agents for affinity capture, treated or untreated microtiter plates, polymer gels, agarose and the like. It will be understood by a skilled practitioner that the method by which the target nucleic acid is bound to the matrix will depend on the particular matrix used. For example, binding to nitrocellulose can be achieved by simple adsorption of nucleic acid to the filter, followed by baking the filter at 75°–80° C. under vacuum for 15 min–2 h. Alternatively, charged nylon membranes can be used that do not require any further treatment of the bound nucleic acid. Beads and microtiter plates that are coated with avidin can be used to bind target nucleic acid that has had biotin attached (via e.g. the use of biotin-conjugated PCR primers). In addition, antibodies can be used to attach target nucleic acid to any of the above solid supports by coating the surfaces with the antibodies and incorporating an antibody-specific hapten into the target nucleic acid.

While immobilization of the target nucleic acid is generally preferred, in some embodiments it may be desirable to hybridize the polymers to the target in solution, i.e., without having bound the target to a support. For example, polymers may be hybridized to the target in solution, and then ligated in solution as part of a technique according to the invention for high throughput screening. Ligation techniques are discussed further below.

In practicing the present invention, the untreated or amplified target nucleic acid, preferably bound to a solid phase or semi-solid phase matrix, is incubated with a mixture of purine and pyrimidine containing polymers (hereinafter also referred to as "polymer" or "polymers"). These polymers are preferably allele-specific oligonucleotides (ASOs). 10–200 ASOs can be pooled for a single hybridization, preferably 50–100, and most preferably 50. The length of individual ASOs may be 16–25 nucleotides, preferably 17 nucleotides in length.

The purine and pyrimidine containing polymers may be synthesized chemically by methods that are standard in the art, e.g., using commercially available automated synthesizers. These polymers may then be radioactively labelled (e.g. end-labelled with $^{32}P$ using polynucleotide kinase) or conjugated to other commonly used "tags" or reporter molecules. For example, fluorochromes (such as FITC or rhodamine), enzymes (such as alkaline phosphatase), biotin, or other well-known labelling compounds may be attached directly or indirectly. Furthermore, using standard methods, a large number of randomly permuted polymers can be synthesized in a single reaction. As detailed below, the present invention does not require that individual hybridizing sequences be determined prior to the hybridization. Rather, the sequence of bound polymers can be determined in a later step.

As described in U.S. patent application Ser. No. 07/957, 205 (filed Oct. 6, 1992, abandoned) and in Shuber et al., 1993, Human Molecular Genetics, 2:153–158, the hybridization reaction can be performed under conditions in which polymers such as those containing different sequences hybridize to their complementary DNA with equivalent strength. This is achieved by: 1) employing polymers of equivalent length; and 2) including in the hybridization mixture appropriate concentrations of one or more agents that eliminate the disparity in melting temperatures among polymers of identical length but different guanosine+ cytosine (G+C) compositions. Agents that may be used for this purpose include without limitation quaternary ammonium compounds such as tetramethylammonium chloride (TMAC).

TMAC acts through a non-specific salt effect to reducing hydrogen-bonding energies between G–C base pairs. At the same time, it binds specifically to A–T pairs and increases the thermal stability of these bonds. These opposing influences have the effect of reducing the difference in bonding energy between the triple-hydrogen bonded G–C based pair and the double-bonded A–T pair. One consequence, as noted above, is that the melting temperature of nucleic acid to nucleic acid hybrids formed in the presence of TMAC is solely a function of the length of the hybrid. A second consequence is an increase in the slope of the melting curve for each probe. Together these effects allow the stringency of hybridization to be increased to the point that single-base differences can be resolved, and non-specific hybridization minimized (Wood et al., 1985, Proc. Natl. Acad. Sci., U.S.A. 82:1585.).

It will be apparent to those skilled in the art that any agent that exhibits these properties can be used, is desired, in practicing the present invention. Such agents can be easily identified by determining melting curves for different test oligonucleotides in the presence and absence of increasing concentrations of the agent. This can be achieved by attaching a target nucleic acid to a solid matrix such as a nylon filter, individually hybridizing radiolabelled oligonucleotides of identical length but different G+C compositions to the filter, washing the filter at increasing temperatures, and measuring the relative amount of radiolabelled probe bound to the filter at each temperature. An agent that, when present in the hybridization and washing steps described above, results in approximately superimposable and steep melting curves for the different oligonucleotides may be used.

In practicing the present invention, the target nucleic acid and polymers can be incubated for sufficient time and under appropriate conditions to achieve maximal specific hybridization and minimal non-specific, i.e. background, hybridization. The conditions to be considered include the concentration of each polymer, the temperature of hybridization, the salt concentration, and the presence or absence of unrelated nucleic acid. It will further be appreciated that the polymers can be separated into at least two groupings, each grouping containing a sufficient number of polymers to allow for hybridization. For example, it may be preferred to divide the total number of polymers of a pool to be hybridized to the nucleic acid samples into groupings of about 50 polymers. Each group of polymers can be hybridized to the nucleic acid immobilized on the support in a sequential manner, but the polymers comprising each group can be hybridized to the nucleic acid at substantially the same time. Additionally, immobilized nucleic acid samples may be hybridized to at least one pool of polymers, the identity of the hybridizing polymers determined, and then the nucleic acid samples hybridized again with the same or different polymer pools.

The concentration of each purine and pyrimidine containing polymer generally ranges from 0.025 to 0.2 pmol per ml of hybridization solution. When polymers of known sequence are used, the optimal concentration for each polymer can be determined by test hybridizations in which the signal-to-noise ratio (i.e. specific vs. non-specific binding) of each polymer is measured at increasing concentrations of labeled polymer. To further reduce background hybridization, oligonucleotides containing the unlabeled non-variant (i.e. wild-type) sequence may be included in the reaction mixture at a concentration equivalent to 1–100 times the concentration of the labelled polymer.

The temperature for hybridization can be optimized to be as high as possible for the length of the polymers being used. This can be determined empirically, using the melting curve determination procedure described above. It will be understood by skilled practitioners that determination of optimal time, temperature, polymer concentration and salt concentration should be done in concert.

It is intended that the hybridized polymers identified by the invention be those that are perfectly hybridized. Methods described above minimize imperfect hybridization. Such methods, however, are not always necessary. In the ligation procedure described in the Examples, imperfect hybrids may form, but perfect hybrids are selectively identified.

Following hybridization, unbound polymers are, if necessary, removed such as by washing the matrix-bound nucleic acid in a solution containing TMAC or similar compounds, under conditions that preserve perfectly matched nucleic acid:polymer hybrids. Washing conditions such as temperature, nature and concentration of salts, and time of washing, are determined empirically as described above. At this stage, the presence of bound polymers may be determined. Different methods for detection will depend upon the label or tag incorporated into the polymers. For example, radioactively labelled or chemiluminescent ASOs that have bound to the target nucleic acids can be detected by exposure of the filter to X-ray film.

Alternatively, polymers containing a fluorescent label can be detected by excitation with a laser or lamp-based system at the specific absorption wavelength of the fluorescent reporter. Still further, polymers can each carry, in addition to the probe sequence, a molecular weight modifying entity (MWME) that is unique for each member of the polymer pool. The MWME does not participate in the hybridization reaction but allows direct identification of the separated polymer by determination of the relative molecular weight by any number of methods. Other methods for detection and identification are described below.

In an optional subsequent step, the bound polymers are separated from the matrix-bound target nucleic acid. Separation may be accomplished by any means known in the art that destabilizes nucleic acid to polymer hybrids, i.e. lowering salt concentration, raising temperature, exposure to formamide, alkali, etc. For example, the bound polymers may be separated by incubating the target nucleic acid-polymer complexes in water, and heating the reaction above the melting temperature of the nucleic acid:polymer hybrids. This obviates the need for further treatment or purification of the separated polymers.

According to this invention, the hybridized polymers, with or without separation from the target nucleic acid, can be identified by a number of different methods that will be readily appreciated by those of skill in the art. By sequencing the polymers, it is possible to correspondingly identify target sequences or genetic alterations in the nucleic acid samples.

The polymers can also be identified by directly labeling them with a unique reporter that provides a detectable signal. Polymers that are directly labeled can be detected using radioactivity, fluorescence, colorimetry, x-ray diffraction or absorption, magnetism, enzymatic activity, chemiluminescence, and electrochemiluminescence, and the like. Suitable labels include fluorophores, chromophores, radioactive atoms (such as $^{32}P$ and $^{125}I$), electron dense reagents, and enzymes that produce detectable products. See L. Kricka, Nonisotopic DNA Probe Techniques, Chapters 1 and 2, Academic Press, 1992 (hereinafter "Kricka").

In addition to direct labeling of polymers, indirect labeling may also be used. Many binding pairs are known in the art for indirect labeling, including, for example, biotin—avidin, biotin—streptavidin, hapten— antihapten antibody, sugar—lectin, and the like. When used with the present invention, one member of a binding pair can be attached to the polymer and the other member of the binding pair directly labeled as described above. Subsequent to hybridization, the polymers that are bound to target nucleic acid sequences may be identified by incubation with the labeled member and subsequent detection of the binding pair-label complex. See, Bioconjugate Chemistry, 1:165–187 (1990); Kricka, Chapters 1 and 2.

The polymers can still further be identified by using unique length markers. That is, by providing polymers having components that contribute a predetermined and unique molecular weight to each individual polymer, in addition to the portions that participate in hydrogen bonding interactions with target nucleic acids, it is possible to identify an individual polymer by molecular weight. See, e.g., Nucleic Acids Res., 22:4527–4534 (1994).

Still further, hybridized polymers can be identified by use of hybridization arrays. In such arrays, purine and pyrimidine containing polymers of predetermined sequence are immobilized at discrete locations on a solid or semi-solid support. When used with the present invention, the sequence of each immobilized polymer comprising the array is complementary to the sequence of a member of the polymer pool. Members of the polymer pool that hybridize with target nucleic acids can be identified after separation from target nucleic acids by rehybridization with immobilized polymers forming the array. The identity of the polymer is determined by the location of hybridization on the array. See, U.S. Pat. No. 5,202,231 and WO 8910977.

Other permutations and possibilities will be readily apparent to those of ordinary skill in the art, and are considered as equivalents within the scope of the instant invention.

More particularly, in one embodiment, the hybridized polymer is directly subjected to sequencing, using a chemical method standard in the art (e.g. Maxam-Gilbert sequencing, Maxam and Gilbert, 1977, Proc. Natl. Acad. Sci., U.S.A., 74:560). This method does not require that polymers be separated from the target nucleic acid prior to sequencing, and, further, is particularly applicable when randomly permuted mixtures of polymers are used.

In another embodiment, the hybridized polymers are identified by enzymatic sequencing (Sanger et al., 1977, Proc. Natl. Acad. Sci., U.S.A., 74:5463). In this case, oligonucleotides are synthesized that contain sequences complementary to the polymers and additional pre-determined co-linear sequences that act as sequence "tags" (see Example 4 below). Separation of the polymers from the target nucleic acid is performed in the presence of a mixture of these complementary, "tagged" oligonucleotides. When incubated under Sanger sequencing conditions (see e.g. Example 5 below), the polymers hybridize to their complementary sequences and act as primers for the sequencing reaction. Determination of the resulting primed sequence "tag" then identifies the polymer(s) present in the reaction.

In a further embodiment, the hybridized polymers are incubated with complementary oligonucleotides that may contain universal primer sequences and/or a sequencing primer sequence with or without an additional "tag" sequence (see Example 4 below). In both cases, initial hybridization of a polymer to its complementary oligonucleotide allows the polymer to serve as the initial primer in a single extension reaction. In one case, the extension product is then used directly as template in a cycle sequencing reaction. Cycle sequencing of the extension products results in amplification of the sequencing products. In designing the complementary oligonucleotides, the sequencing primer is oriented so that sequencing proceeds through the polymer itself, or, alternatively, through the "tag" sequence.

In the second case, the extension product includes a universal primer sequence and a sequencing primer sequence. This extension product is then added to a linear amplification reaction in the presence of universal primer. The oligonucleotides containing complementary sequences to bound polymers are therefore selectively amplified. In a second step, these amplified sequences are subjected to Sanger sequencing, using the built-in sequencing primer sequence. In this case, the sequencing primer is placed immediately upstream of a "tag" sequence as above. Thus, determination of the "tag" sequence will identify the colinear polymer sequence.

In practicing the present invention, it is not necessary to determine the entire sequence of the polymer or of a complementary tagged oligonucleotide. It is contemplated that 1, 2, or 3 sequencing reactions (instead of the four needed to obtain a complete sequence) will be effective in producing characteristic patterns (similar to "bar codes") to allow the immediate identification of individual polymers. This approach is applicable to manual sequencing methods using radioactively labelled polymers, which produce analog or digitized autoradiograms, as well as to automated sequencing methods using non-radioactive reporter molecules, which produce digitized patterns. In either case, comparisons to an established data base can be performed electronically. Thus, by reducing the number of required sequencing reactions, the methods of the present invention facilitate the economical analysis of multiple samples, and of multiple nucleic acid sequences or genetic alterations within each sample.

The present invention accommodates the simultaneous screening of a large number of potential polymers in a single reaction. In practice, the actual number of polymers that are pooled for simultaneous hybridization is determined according to the diagnostic need. For example, in cystic fibrosis (CF), one particular mutation (Δ508) accounts for more than 70% of CF cases. Thus, a preliminary hybridization with a labelled or tagged Δ508-specific polymer according to the present methods, followed by detection of the bound polymer, will identify and eliminate Δ508 alleles. In a second ("phase two") hybridization, a large number of polymers encoding other, less frequent, CF alleles are utilized, followed by separation and sequencing as described above.

In other clinical situations, however, a single mutation that appears with as high a frequency as the Δ508 mutation in CF does not exist. Therefore, pools of polymers are determined only by the number of independent hybridizations that would be needed in a phase two analysis on a pool positive sample.

In addition, in current clinical practice, different clinical syndromes, such as cystic fibrosis, β-thalassemia, and Gaucher's disease, are screened independently of each other. The present invention, by contrast, accommodates the simultaneous screening of large numbers of nucleic acid samples from different sources, including different mammals, with a large number of polymers that are complementary to mutations in more than one potential disease-causing gene.

In the same manner, when clinical indicators suggest infection by a foreign agent or microorganism, the present invention provides for simultaneous screening for a large number of potential foreign nucleic acids. Furthermore, particular strains, variants, mutants, and the like of one or more microorganisms can also be distinguished by employing appropriate polymers in the screening.

The methods of the present invention also make it possible to define potentially novel mutant alleles carried in the nucleic acid of a patient or an invading microorganism, by the use of randomly permuted polymers in phase one or phase two screening. In this embodiment, separation of the bound polymers, followed by sequencing, reveals the precise mutant sequence.

This invention further contemplates a kit for carrying out high-throughput screening of nucleic acid samples according to this invention. The kit will include, in packaged combination, at least the following components: a support, a multiplicity of purine and pyrimidine containing polymers, appropriate labeling components, and enzymes and reagents required for polymer sequence determination.

Model Systems of the Invention

Seven different gene targets, representing eight different diseases, were chosen as a model system for complex mutation detection (Table 1). A total of 106 different mutations were analyzed in a single hybridization and detection procedure, referred to as MASDA 106. Although large numbers of mutations have been identified within the majority of disease genes listed, for the purposes of this study a selected number of these mutations were used (Table 1 columns 3 and 4). The specific mutations chosen within each disease gene represented the most clinically relevant for diagnostic applications The largest number of mutations analyzed resided within the CFTR gene. In addition to the most frequently detected mutations within a CF patient population, additional point mutations were included that lead to premature translation termination, and subsequently a truncated protein product. A total of 33 different amplification products were needed in order to interrogate for the presence or absence of the 106 different mutations (Table 1 column 5). It is important to note that amplifications were performed in a disease-specific manner only. In other words, if a patient was suspected to be a cystic fibrosis carrier, the DNA sample was amplified for the cystic fibrosis gene only.

The specific mutations examined within each disease gene are shown in Tables 1–8. These tables also include the size (bp) of regions amplified, and the primers used for each amplification.

Figure 10:
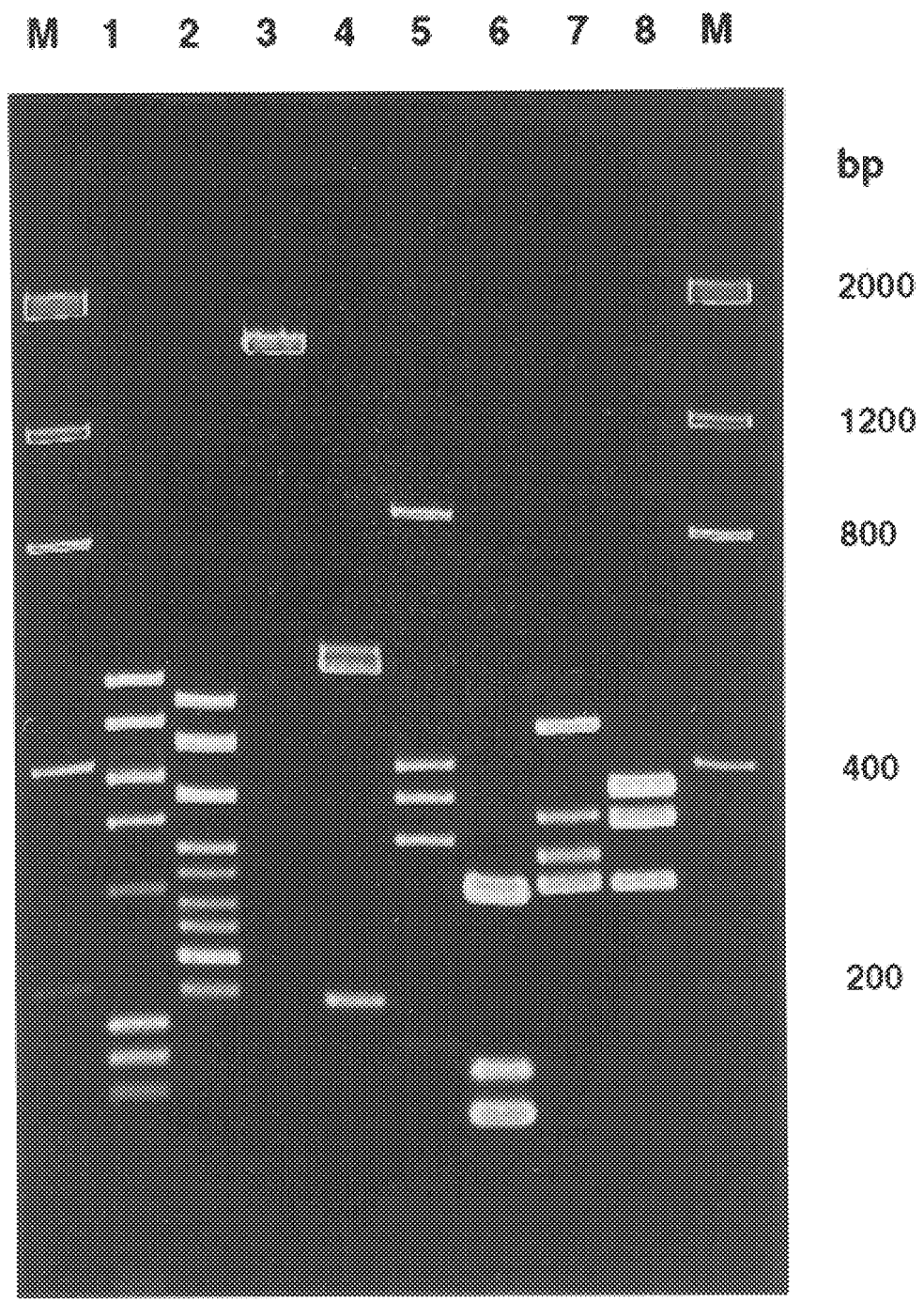
FIG. 10 shows disease gene loci amplified by multiplex PCR for MASDA assay. DNA samples (2 mg) were amplified in multiplexes specific for one of seven different genes and analyzed by gel electrophoresis. M=ΦX174/HaeIII Molecular weight marker: 1=Eight amplicon multiplex within the CFTR gene. 2=Nine amplicon multiplex within the CFTR gene. 3=Single amplicon within the β-globin gene. 4=Two amplicon multiplex within the HEXA gene. 5=(3+1) multiplex (three amplicon multiplex+one independent amplicon) for the GCR gene. 6=Three amplicon multiplex within the ASPA gene. 7=Four amplicon multiplex within the BRCA1 gene. 8=Three amplicon multiplex within the FACC gene.

Disease Specific Target Amplifications

Where applicable, multiplex PCR was performed to reduce the number of PCR reactions needed (Table 1, column 5). A total of 9 reactions facilitated amplification of 33 different loci. All single or multiplex PCR reactions were performed in a disease-specific manner. In other words, DNA samples were amplified for the relevant disease gene only, and not for all loci examined in the assay. Examples of the various disease-specific amplification products are shown in FIG. 10. In order to include 66 CF mutations within the study discussed herein, 17 different regions within the CFTR gene were amplified using two multiplex PCR reactions (FIG. 10 lanes 1 and 2). Amplicon sizes ranged from 130–510 bp. A single amplification product of 1600 bp was sufficient to include 14 β-thalassemia and two sickle cell anemia associated mutations within the β-globin (FIG. 10 lane 4). To examine Canavans-associated mutations 3-plex amplification reactions were performed (FIG. 10 lane 6). A separate 4-plex amplification was performed for five Breast Cancer Susceptibility-related mutations (FIG. 10 lane 7) and a single 3-plex amplification for Fanconi Anemia-associated mutations (FIG. 10 lane 8). For Gauchers disease, the GCR pseudogene neccesitated a 3-plex amplification and an independent, single amplicon amplification. For convenience of analysis, aliquots from both reactions were pooled and electrophoresed in the same lane of the analytical gel (FIG. 10 lane 5).

Mutation Detection

Figure 11:
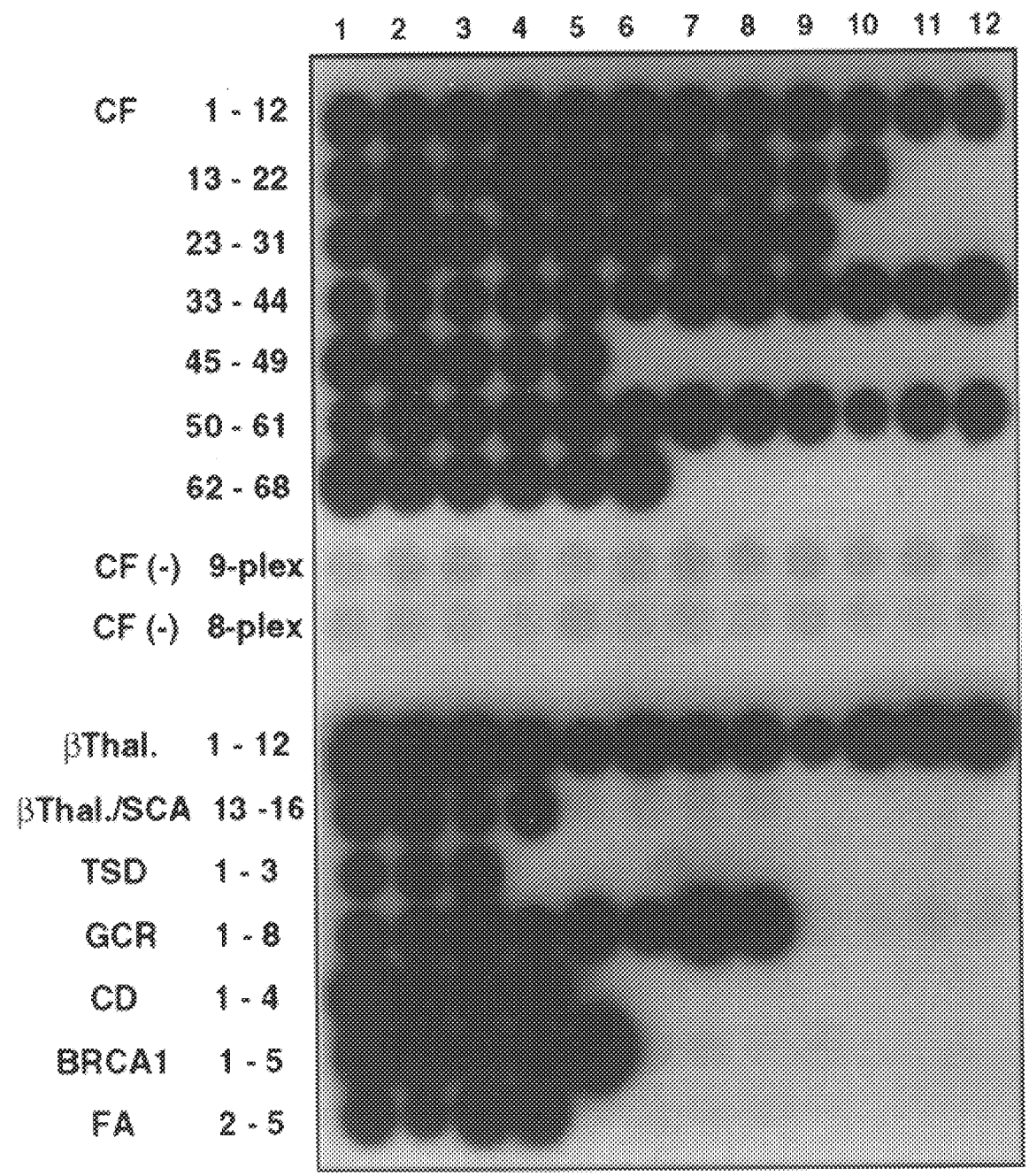
FIG. 11 shows simultaneous detection of 106 different mutations within 33 target regions from seven different genes in a single hybridization assay. Rows 1–7=Detection of 66 CFTR mutations present in cystic fibrosis (CF). Rows 8–9=Negative control samples for cystic fibrosis (CF–) mutations. Rows 10–11=Detection of 14 β-globin mutations in β-thalassemia (βThal.) and 2 β-globin mutations in sickle cell anemia (SCA). Row 12=Detection of 3 HEXA mutations present in Tay Sachs (TSD). Row 13=Detection of 8 GCR mutations present in Gaucher's disease (GCR). Row 14=Detection of 4 ASPA mutations present in Canavan Disease (CD). Row 15=Detection of 5 BRCA 1 mutations present in breast cancer (BRC). Row 16=Detection of 4 FACC mutations present in *Fanconi anemia* (FA). Disease-specific negative control samples follow the positive samples in Rows 11–16.

In order to simultaneously analyze large numbers of samples for the mutations listed in Table 1, the standard forward dot blot format was employed and a single multiplex hybridization was performed (FIG. 11). Although the percent G–C content of the 106 mutation-specific oligonucleotides ranged between 18% and 76%, the use of tetramethylammonium chloride (TMAC) (31) allowed all 106 mutation-specific oligonucleotides to be mixed together and hybridized in a single pool. Furthermore, the presence of TMAC in the hybridization and wash solutions allowed the hybridization and washes to be performed at the same temperature. As seen in FIG. 11, only the 106 mutation-specific positive control samples generated signals upon autoradiography with no significant non-specific signal exhibited by the negative control samples. Overall signal intensities and signal-to-noise-ratios generated for the different mutation-specific positive control samples were optimized by adjusting concentrations of each mutation-specific oligonucleotide within the hybridization.

Mutation Identification

Figures 3A, 3B:
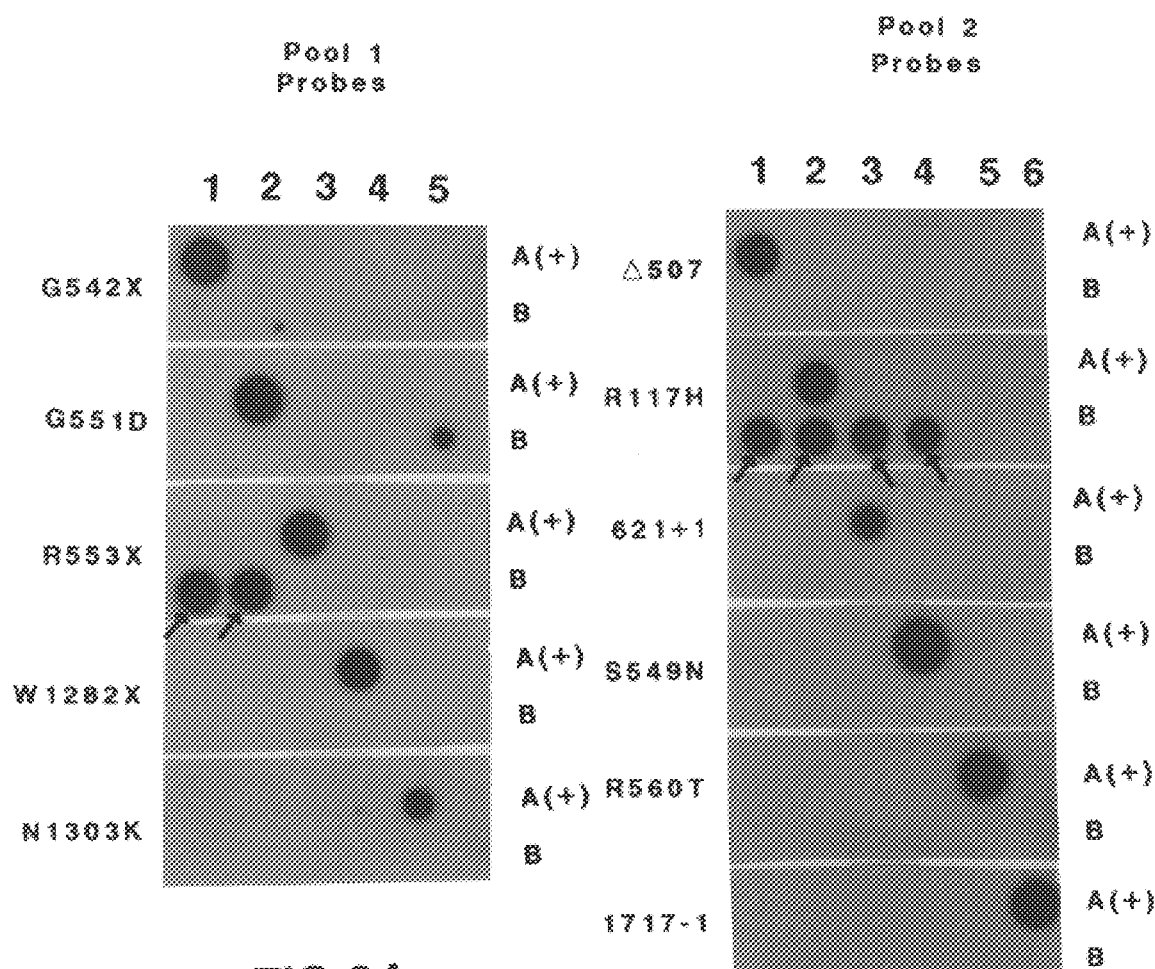
FIGS. 3A and 3B show the identification of specific mutations in pool-positive samples identified in FIG. 1. The top row of each filter contains positive control samples for ASOs in pool 1 and pool 2 as indicated. Pool 1, lane 1, G542X; lane 2, G551D; lane 3, R553X; lane 4, W1282X; lane 5, N1303K. Pool 2, lane 1, Δ507; lane 2, R117H; lane 3, 621+1 G->T; lane 4, S549N; lane 5, R560T; lane 6, 1717-1 G->A. Row B contains pool-1 or pool-2 positive patient samples. Pool 1, lanes 1 and 2 contain sample 4, lanes D and E from FIG. 1. Pool 2, lanes 1 and 2 contains sample 3, lanes D and E from FIG. 2. Lanes 3 and 4 contain sample 5, lanes D and E from FIG. 2.
Figure 12:
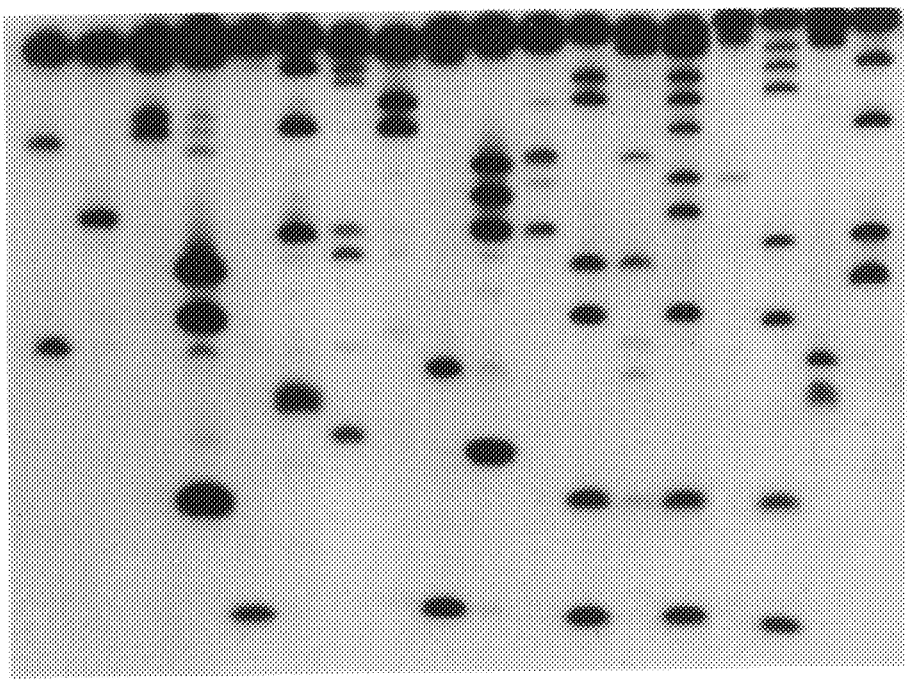
FIG. 12 shows the band patterns generated by chemical cleavage of eluted ASOs and reveals the identity of the mutation. C=C cleavage reaction; G=G cleavage reaction.

The specific mutation present within any pool-positive sample was identified by eluting the hybridized oligonucleotide from the sample DNA and directly interrogating the oligonucleotide sequence. In one scheme, the eluted oligonucleotides were attached to a solid support, G and C base specific chemical modification reactions were performed, and the reaction products separated by polyacrylamide gel electrophoresis (32). FIG. 12 represents an example of the CG limited sequencing fingerprints produced from some of the oligonucleotides eluted from the pool-positive control samples in FIG. 3 (CF30, CF31, TS1, TS2, TS3, BT2, BT3*, BT6 and BT7). Each eluted oligonucleotide shown in FIG. 12 generated a characteristic fingerprint which unambiguously identified the specific mutation present in the pool-positive sample DNA. Unique band patterns were generated or each of 106 ASOs. Sequence analysis of all 106 eluted oligonucleotides verified that a positive result from the single pooled hybridization represented specific oligonucleotide hybridization with no significant cross hybridization between different probes. In addition, one sample containing two β-globin mutations (FIG. 12, lane BT3*) generated a unique fingerprint made up of two superimposed oligonucleotide-specific band patterns. This demonstrated that a compound heterozygote genotype was readily identified using this technique.

Figure 13:
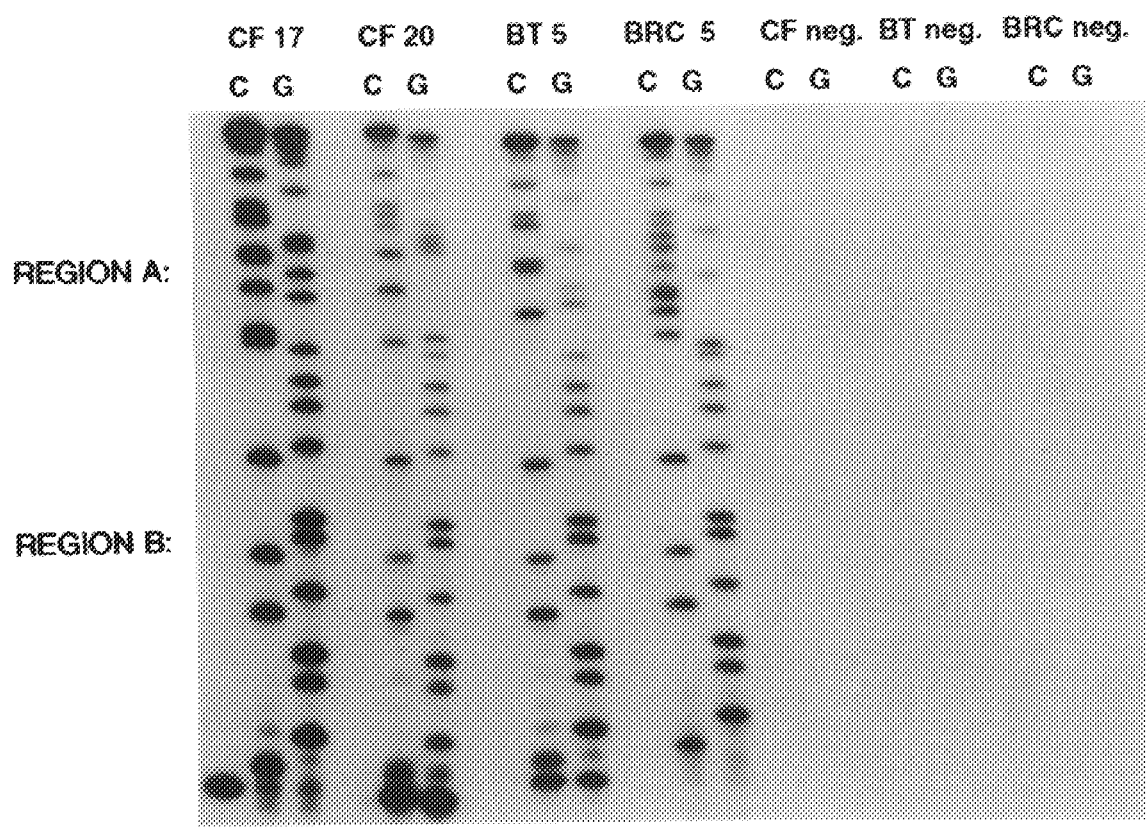
FIG. 13 shows the band patterns generated by an enzymatic sequencing procedure reveal the identity of the mutation. The ASO(s) eluted from mutation-positive samples were used to prime cycle sequencing reactions in a complex mixture of templates. Each template contained a region complementary to a specific ASO (the priming site), a common "stuffer region" (Region B) and a downstream mutation-specific identifier sequence (Region A). With limited C and G sequencing (Lanes C and G for each sample), the fingerprint generated from the mutation-specific identifier sequence unequivocally identified the specific ASO, and therefore the mutation present in the target DNA. CF=cystic fibrosis; BT=β-thalassemia; BRC=Breast Cancer Susceptibility BRCA1 gene. Lane 1=CF17 mutation; Lane 2=CF 20 mutation; Lane 3=BT5 mutation; Lane 5=CF negative control; Lane 6=BT negative control; Lane 7=BRC negative control.

In addition to the chemical modification and cleavage procedure, an enzymatic protocol for eluted oligonucleotide identification was developed. This procedure involved using the eluted mutation specific oligonucleotide as a primer in a cycle sequencing reaction. The eluted oligonucleotide was added to a cycle sequencing reaction mix containing a mixture of synthetic (77-mer) templates. Each synthetic template contained a different priming sequence complementary to one of the mutation-specific oligonucleotides present in the pooled hybridization reaction, and a downstream specific identifier sequence to generate unique, mutation-specific fingerprints identifying the eluted ASO. FIG. 13 is an example of the C and G band patterns generated from cycle sequencing reactions utilizing oligonucleotides eluted from positive (mutant genotype CF17, CF20, BT5 and BRC5) and negative (normal genotype CF neg., BT neg., and BRC neg.) control samples. Each reaction performed with oligonucleotides eluted from posItive control samples (FIG. 13 lanes 1–4) generated a common band pattern contained within all synthetic templates (Region B) followed by a mutation-specific fingerprint (Region A). The pattern observed In the mutation-specific fingerprints allowed unequivocal identification of the corresponding ASO primer, and consequently the specific mutation present in the patient sample. No band patterns were observed when cycle sequencing reactions were performed with eluates from negative control samples (FIG. 13 lanes 5–7).

Large Scale Sample Analysis

Figure 14:
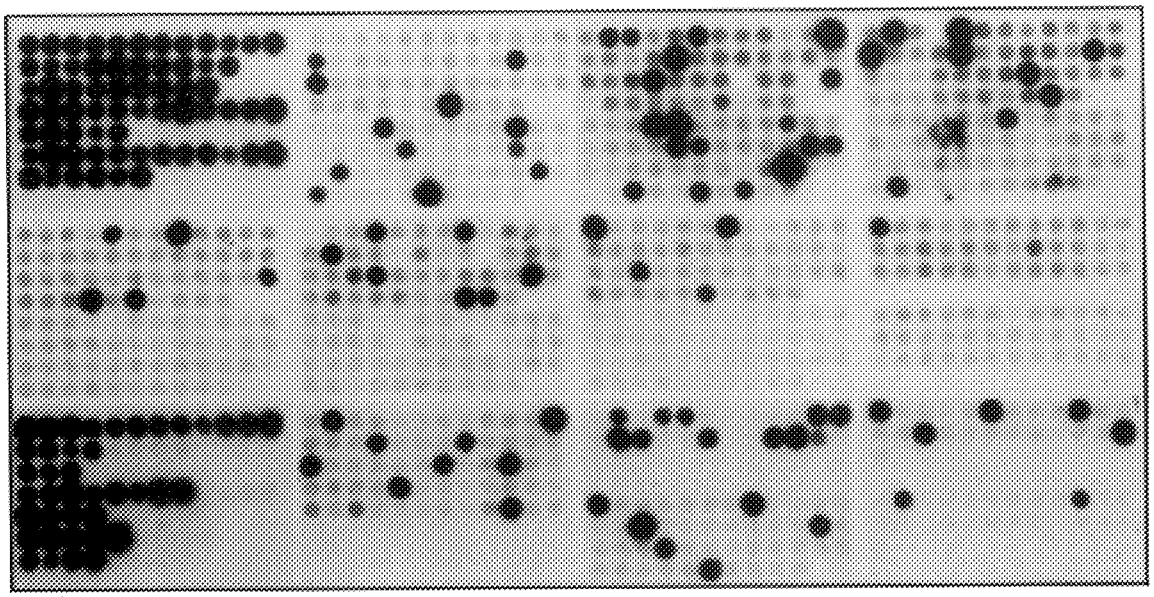
FIG. 14 shows the simultaneous detection of 106 different mutations in over 500 different patient samples in a single ASO hybridization assay.

To validate the invention MASDA procedure, a blinded analysis was performed to assess the ability of the MASDA technique to identify mutations as envisioned in the diagnostic setting. FIG. 14 represents the hybridization results generated from analyzing >500 different DNA samples for the presence of 106 different mutations, in a single hybridization assay. All samples known to carry one of the 106 different mutations were correctly identified as pool-positive in the multiplex hybridization (FIG. 14). The specific mutations were correctly identified within each pool-positive sample by performing the chemical modification and cleavage procedure. It is significant to note that no increase in non-specific background was observed when sample throughput was increased to more than 500 samples in a single hybridization assay.

The following examples are intended to further illustrate the present invention without limiting the invention thereof.

EXAMPLE 1

Mutation-Positive Genomic DNA and Genomic Negative DNA Samples

A) Preparation of Sample DNA from Blood

Whole blood samples collected in high glucose ACD Vacutainers™ (yellow top) were centrifuged and the buffy coat collected (33). The white cells were lysed with two washes of a 10:1 (v/v) mixture of 14 mM NH4Cl and 1 mM NaHCO3, their nuclei were resuspended in nuclei-lysis buffer (10 mM Tris, pH 8.0, 0.4M NaCl, 2 mM EDTA, 0.5% SDS, 500 µg/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-Hcl, pH 7.5, 1 mM EDTA.).

B) Preparation of Sample DNA from Buccal Cells

Buccal cells were collected on a sterile cytology brush (Scientific Products) or female dacron swab (Medical Packaging Corp.) by twirling the brush or swab on the inner cheek for 30 seconds. DNA was prepared as follows, immediately or after storage at room temperature or at 4° C. The brush or swab was immersed in 600 µl of 50 mM NaOH contained in a polypropylene microcentrifuge tube and vortexed. The tube, still containing the brush or swab, was heated at 95° C. for 5 min, after which the brush or swab was carefully removed. The solution containing DNA was then neutralized with 60 µl of 1M Tris, pH 8.0, and vortexed again (Mayall et al., J.Med.Genet. 27:658, 1990). The DNA was stored at 4° C.

C) Cloned Positive Control DNA Samples

When mutation-positive genomic DNA was not available, oligonucleotides representing 40 bp of endogenous gene sequence including the mutation were synthesized, cloned into pGem®-3Zf(+) vectors (Promega Corporation, Madison, Wis.), and the presence of the mutation on each clone verified by sequencing.

D) Amplification of Target DNA Prior to Hybridization DNA Amplifications

As a model system for complex mutation detection, mutations were selected from 33 regions in seven different genes. The genes included the cystic fibrosis transmembrane conductance regulator gene (CFTR), the β-globin gene, the Tay-Sachs hexosaminidase gene (HEXA), the Gaucher gene (GCR), the Canavan aspartoacylase gene (ASPA), the breast cancer susceptibility gene (BRCA1) and the Fanconi Anemia Complementation Group C gene (FACC).

PCR amplifications were performed using 1–2 µg of genomic DNA or 10 ng of plasmid DNA in 100 ml of reaction buffer containing 10 mM TrisHCl pH 8.3, 50 mM KCl, 1.5 mM MgCl$_2$, 200 mM dNTPs and 0.05–0.1 units/µl Taq polymerase (Perkin-Elmer, Norwalk, Conn.). For the different disease gene amplifications, the concentration of primers ranged from 0.2–1.6 mM.

For DNA amplifications involving simultaneous multiplexes of 3 or more amplicons (CFTR 8-plex and 9-plex, ASPA 3-plex, BRCA1 4-plex, and FACC 3-plex) the primers were chimeras of a sequence-specific region with a common "universal primer sequence" (UPS) as described by Shuber et al. (33). These primers facilitated rapid multiplex development and consistently robust amplifications.

DNA amplifications were performed using a Perkin-Elmer 9600 Thermal Cycler (Perkin-Elmer, Norwalk, Conn.). For CFTR, HEXA, ASPA, BRCA1 AND FACC, the amplifications were carried out for 28 cycles with ramping (94° C./10 sec. hold with 48 sec. ramp, 60° C./10 sec. hold with 36 sec. ramp, 72° C./10 sec. hold with 38 sec. ramp) with a final 74° C. hold for 5 minutes before cooling. For β-globin and GCR, the amplification program consisted of 28 cycles with a 55° C. anneal (94° C./10 sec. hold, 55° C./10 sec. hold, 74° C./10 sec. hold) with a final 74° C. hold for 5 minutes before cooling.

Amplification products were analyzed by 2% agarose gel electrophoresis followed by ethidium bromide staining and visualization on a UV transilluminator (Fotodyne, New Berlin, Wis.)

E) Binding of DNA to a Solid Matrix

8 μl of the amplified DNA solution prepared as in D) were added to 50 μl of a denaturing solution (0.5 mM NaOH, 2.0M NaCl, 25 mM EDTA) and spotted onto nylon membrane filters (INC Biotrans). The DNA was then fixed to the membranes by baking the filters at 80° C. for 15 minutes under vacuum.

EXAMPLE 2

Hybridization with Allele-Specific Oligonucleotides (ASOs)

Specific Mutations Examined in the MASDA 106 Hybridization Assay

Mutations from 7 different genes were selected as candidates for a complex mutation detection assay. The 106 mutations examined included point mutations, deletions and insertions. Details of the selected mutations and gene amplifications are listed in Tables 1–8.

TABLE 1

Model System Detailing the Diseases and Mutations Examined using the MASDA Technology

| Disease | Gene | Number of Known Mutations | Number of ASO Probes | Number of PCR Reactions |
|---|---|---|---|---|
| Cystic Fibrosis (CF) | CFTR | >500 | 66 CF 1–31 CF 33–68 | 2 8-plex and 9-plex |
| β-Thalassemia (BT) | β-globin | >90 | 14 | 1 |
| Sickle Cell (SCA) | β-globin | 2 | 2 | Same amplicon as β-Thalassemia |
| Tay-Sachs (TS) | Hexosaminidase A (HEXA) | >28 | 3 | 1 (2-plex) |
| Gaucher (GCR) | Glucocerebrosidase (GCR) | >35 | 8 | 2 (3-plex + 1) |
| Canavan Disease (CD) | Aspartoacylase (ASPA) | >4 | 4 | 1 (3-plex) |
| Breast Cancer Susceptibilit | BRCA1 | >250 | 5 | 1 (4-plex) |
| Fanconi Anemia (FA) | Fanconi anemia complementation C (FACC) | >8 | 4 | 1 (3-plex) |
| MASDA 106 | | | 106 | 9 |

TABLE 2a

Cystic Fibrosis Mutations Examined in CFTR 8-plex Amplifications

| Exon | Amplicon Size (bp) | Primers | Mutation Number | Mutation Name |
|---|---|---|---|---|
| 12 | 510 | 16UPCFX12F | CF 26 | 1898+1 |
|  |  | 16UPCFX12R | CF 36 | 1812 − 1 |
|  |  |  | CF 37 | Y563D |
|  |  |  | CF 38 | P574H |
| 19 | 450 | UP3CFEX19F | CF 23 | 3849 + 4 |
|  |  | UP3CFEX19R | CF 27 | R1162X |
|  |  |  | CF 31 | 3659dC |
|  |  |  | CF 42 | R1158X |
|  |  |  | CF 43 | S1196X |
|  |  |  | CF 44 | I1203V |
|  |  |  | CF 45 | Q1238X |
|  |  |  | CF 46 | 3662dA |
|  |  |  | CF 47 | 3750dAG |
|  |  |  | CF 48 | 3791dC |
|  |  |  | CF 49 | 3821dT |
| 9 | 375 | 15UPCFX9F | CF 28 | A455E |
|  |  | 15UPCFX9R |  |  |
| 13 | 335 | UP3CFEX13F | CF 29 | 2184dA |
|  |  | UP3CFEX13R | CF 39 |  |
|  |  |  | CF 40 | K710X |
| 3 | 270 | UP3CFEX3F | CF 30 | G85E |
|  |  | UP3CFEX3R | CF 33 | E60X |
|  |  |  | CF 34 | 405 + 1 |
| 5 | 172 | UP3CFEX5F | CF 25 | 711 + 1 |
|  |  | 15UPCFX5R | CF 35 | G178R |
| 14b | 150 | 15UCFX14bF | CF 24 | 2789 + 5 |
|  |  | 15UCFX14bR |  |  |
| 16 | 130 | 16UPCFX16F | CF 41 | 3120 + G |
|  |  | 16UPCFX16R |  |  |

TABLE 2b

Cystic Fibrosis Mutations Examined in CFTR 9-plex Amplifications

| Exon | Amplicon Size (bp) | Primers | Mutation Number | Mutation Name |
|---|---|---|---|---|
| Int 19 | 480 | 15UCFIN19F | CF 8 | 3849 + 10 |
|  |  | 15UCFIN19R |  |  |
| 21 | 421 | REUPCFX21F | CF 5 | N1303X |
|  |  | 15UPCFX21R | CF 67 | W1310X |
|  |  |  | CF 68 | W1316X |
| 15 | 361 | UP3CFEX15F | CF 60 | Q890X |
|  |  | UP3CFEX15R | CF 61 | 2869 + G |
|  |  |  | CF 62 | 2909dT |
| 4 | 307 | 15UPCFX4F | CF 6 | R117H |
|  |  | 15UPCFX4R | CF 10 | 621 + 1 |
|  |  |  | CF 21 | Y122X |
|  |  |  | CF 50 | 444dA |
|  |  |  | CF 51 | 556dA |
|  |  |  | CF 52 | 574dA |
| 17b | 285 | L15UCF17BF | CF 16 | Y1092X |
|  |  | L15UCF17BR | CF 64 | W1089X |
|  |  |  | CF 65 | 3358dAC |
| 7 | 260 | REUPCFX7F | CF 12 | 1078dT |
|  |  | REUPCFX7R | CF 17 | R347H |
|  |  |  | CF 18 | R347P |
|  |  |  | CF 20 | R334W |
|  |  |  | CF 53 | G330X |
|  |  |  | CF 54 | R352Q |
|  |  |  | CF 55 | S364P |
| 11 | 240 | 15UPCFX11F | CF 1 | G542X |
|  |  | 15UPCFX11R | CF 2 | G551D |
|  |  |  | CF 9 | R553X |
|  |  |  | CF 11 | 1717-1 |
|  |  |  | CF 15 | S549R |
|  |  |  | CF 19 | R560T |
|  |  |  | CF 22 | S549N |
|  |  |  | CF 59 | A559T |

TABLE 2b-continued

Cystic Fibrosis Mutations Examined in CFTR 9-plex Amplifications

| Exon | Amplicon Size (bp) | Primers | Mutation Number | Mutation Name |
|---|---|---|---|---|
| 10 | 215 | 15UPCFX10F | CF 7 | DI507 |
|  |  | 15UPCFX10R | CF 13 | Q493X |
|  |  |  | CF 14 | V520F |
|  |  |  | CF 56 | 508C |
|  |  |  | CF 57 | C524X |
|  |  |  | CF 58 | 1677dTA |
| 20 | 195 | 15UPCFX20F | CF 3 | W1282X |
|  |  | 15UPCFX20R | CF 4 | 3905 + T |
|  |  |  | CF 66 | S1255X |

TABLE 3

β-thalassemia and Sickle Cell Anemia Mutations Examined in β-globin Gene Amplifications

| Exon | Amplicon Size (bp) | Primers | Mutation # | Mutation Name |
|---|---|---|---|---|
| 1–3 | 1600 | GH260 | BT 1 | IVS1-1 |
|  |  | GH283 | BT 2 | IVS1-6 |
|  |  |  | BT 3 | IVS1-5 |
|  |  |  | BT 4 | IVS-110 |
|  |  |  | BT 5 | NONS-39 |
|  |  |  | BT 6 | IVS2-1 |
|  |  |  | BT 7 | IVS-745 |
|  |  |  | BT 8 | COD8/9 |
|  |  |  | BT 9 | IVS-654 |
|  |  |  | BT 10 | 41/42 |
|  |  |  | BT 11 | -29 |
|  |  |  | BT 12 | 71/72 |
|  |  |  | BT 13 | COD24 |
|  |  |  | BT 14 | -88 |
| 1–3 | 1600 | GH260 | SCA 1 | HbS |
|  |  | GH283 | SCA 2 | HbC |

TABLE 4

Tay-Sachs Mutations Examined in HEXA Gene Amplifications

| Exon | Amplicon Size (bp) | Primers | Mutation # | Mutation Name |
|---|---|---|---|---|
| 11/12 | 530 | TSEX11F | TS 2 | Ex11 4 bp Ins |
|  |  | TSEX12R | TS 3 |  |
| 7 | 190 | TSEX7F | TS 1 | G269S |
|  |  | TSEX7R |  |  |

TABLE 5

Gaucher Mutations Examined in GCR Gene Amplifications

| Exon | Amplicon Size (bp) | Primers | Mutation # | Mutation Name |
|---|---|---|---|---|
| 10/11 | 871 | GCRDF | GCR5 | 1448 |
|  |  | GCRDR | GCR 6 | 1604 |
|  |  |  | GCR 8 |  |
| 2 | 358 | 84IVSF | GCR 3 | 84GG |
|  |  | 84IVSR | GCR 4 | IVS2 + 1 |
| 9 | 319 | 1226F | GCR 1 | 1297 |
|  |  | 1226R | GCR 2 | 1226 |
|  |  |  | GCR 7 | 1342 |

TABLE 6

Canavan Mutations Examined in ASPA Gene Amplifications

| Exon | Amplicon Size (bp) | Primers | Mutation # | Mutation Name |
|---|---|---|---|---|
| 6 | 274 | CD6F | CD 3 | E285A |
|  |  | CD6R | CD 4 | A305E |
| 5 | 151 | CD5F | CD 2 | Y231X |
|  |  | CD5R |  |  |
| Int2/Ex3 | 147 | CDInt2F | CD 1 | 433-2 |
|  |  | CDEx3R |  |  |

TABLE 7

Breast Cancer Susceptibility Mutations Examined in BRCA1 Amplifications

| Exon | Amplicon Size (bp) | Primers | Mutation # | Mutation Name |
|---|---|---|---|---|
| 20 | 450 | BRCA20F | BRC 4 | 5382 + C |
|  |  | BRCA20R |  |  |
| 21 | 315 | BRCA21F | BRC 5 | M1775R |
|  |  | BRCA21R |  |  |
| 2 | 290 | BRCA2F | BRC 1 | 185dAG |
|  |  | BRCA2R |  |  |
| 5 | 270 | BRCA5F | BRC2 | C61G |
|  |  | BRCA5R | BRC 3 | C64G |

TABLE 8

Fanconi Anemia Mutations Examined in FACC Amplifications

| Exon | Amplicon Size (bp) | Primers | Mutation # | Mutation Name |
|---|---|---|---|---|
| 1 | 366 | FA1F | FA 2 | Q13X |
|  |  | FA1R |  |  |
| 6 | 329 | FA6F | FA 4 | R185X |
|  |  | FA6R | FA 5 | D195V |
| 4 | 274 | FA4F | FA 3 | IVS4 + 4 |
|  |  | FA4R |  |  |

Oligonucleotide Pools

Allele-specific oligonucleotides (ASOs) were 17-mers synthesized and HPLC-purified by Operon Technologies (Alameda, Calif.). All oligonucleotides were quantitated by spectrophotometry and tested in independent hybridizations before being pooled. Specified amounts of individual ASOs were combined into a pool of 106 ASOs so that the pool would contain the required amount of each specific ASO determined to be optimal for the pool hybridization. Aliquots of pooled ASOs were lyophilized and stored at −20° C.

Examples of ASOs representing known cystic fibrosis (CF) mutations are set forth below.

| ASO | Sequence (17-mer) |  |
|---|---|---|
| ΔF508M | 5'ACA/CCA/ATG/ATA/TTT/TC 3' | SEQ ID NO: 1 |
| G542XM | 5'ATT/CCA/CCT/TCT/CAA/AG 3' | SEQ ID NO: 2 |
| G551DM | 5'CTC/GTT/GAT/CTC/CAC/TC 3' | SEQ ID NO: 3 |
| R553XM | 5'CTC/ATT/GAC/CTC/CAC/TC 3' | SEQ ID NO: 4 |
| W1282XM | 5'CTT/TCC/TTC/ACT/GTT/GC 3' | SEQ ID NO: 5 |
| N1303KM | 5'TCA/TAG/GGA/TCC/AAC/TT 3' | SEQ ID NO: 6 |
| Δ1507M | 5'ACA/CCA/AAG/ATA/TTT/TC 3' | SEQ ID NO: 7 |
| R117HM | 5'CGA/TAG/AGT/GTT/CCT/CC 3' | SEQ ID NO: 8 |
| 621+1M | 5'GCA/AGG/AAG/TAT/TAA/CT 3' | SEQ ID NO: 9 |
| S549NM | 5'CTC/GTT/GAC/CTC/CAT/TC 3' | SEQ ID NO: 10 |

-continued

| ASO | Sequence (17-mer) | |
|---|---|---|
| R560TM | 5'TAT/TCA/CGT/TGC/TAA/AG 3' | SEQ ID NO: 11 |
| 1717−1M | 5'GGA/GAT/GTC/TTA/TTA/CC 3' | SEQ ID NO: 12 |
| 3849+10M | 5'ACT/CAC/CAT/TTT/AAT/AC 3' | SEQ ID NO: 13 |
| 3905+TM | 5'GTA/GTC/TCA/AAA/AAA/GC 3' | SEQ ID NO: 14 |
| R347PM | 5'GTG/ACC/GCC/ATG/GGC/AG 3' | SEQ ID NO: 15 |
| 1078dTBM | 5'CAC/CAC/AAG/AAC/CCT/GA 3' | SEQ ID NO: 16 |
| 2789+5GAM | 5'GGA/ATA/TTC/ACT/TTC/CA 3' | SEQ ID NO: 17 |
| 3849+4CM | 5'GCA/GTG/TTC/AAA/TCC/CA 3' | SEQ ID NO: 18 |
| 711+1GTM | 5'CAT/AAT/TCA/TCA/AAT/TT 3' | SEQ ID NO: 19 |
| R1162XM | 5'CTC/AGC/TCA/CAG/ATC/GC 3' | SEQ ID NO: 20 |
| 1898+1GAM | 5'CAT/ATC/TTT/CAA/ATA/TT 3' | SEQ ID NO: 21 |
| 3659dCM | 5'CTT/GTA/GGT/TTA/CCT/TC 3' | SEQ ID NO: 22 |
| G85EM | 5'GAT/TTC/ATA/GAA/CAT/AA 3' | SEQ ID NO: 23 |
| 2184dAM | 5'GAT/TGC/TTT/TTG/TTT/CT 3' | SEQ ID NO: 24 |
| A455EM | 5'AAC/CTC/CAA/CAA/CTG/TC 3' | SEQ ID NO: 25 |
| R334WM | 5'TTC/CAG/AGG/ATG/ATT/CC 3' | SEQ ID NO: 26 |
| Y122XBM | 5'AGT/TAA/ATC/GCG/ATA/GA 3' | SEQ ID NO: 27 |
| S549RBM | 5'TCC/CCT/CAG/TGT/GAT/TC 3' | SEQ ID NO: 28 |
| Q493XM | 5'ACT/AAG/AAC/AGA/ATG/AA 3' | SEQ ID NO: 29 |
| V520FM | 5'GAT/GAA/GCT/TCT/GTA/TC 3' | SEQ ID NO: 30 |
| Y1092XM | 5'ACA/GTT/ACA/AGA/ACC/AG 3' | SEQ ID NO: 31 |
| R347HM | 5'GTG/ACC/GCC/ATG/TGC/AG 3' | SEQ ID NO: 32 |

Examples of ASOs representing wild-type or normal sequences are set forth below.

| ASO | Sequence (17-mer) | |
|---|---|---|
| ΔF508N | 5'CAT/AGG/AAA/CAC/CAA/AG 3' | SEQ ID NO: 33 |
| G542XN | 5'ATT/CCA/CCT/TCT/CCA/AG 3' | SEQ ID NO: 34 |
| G551DN | 5'CTC/GTT/GAC/CTC/CAC/TC 3' | SEQ ID NO: 35 |
| R553XN | See G551 DN sequence | |
| W1282XN | 5'CTT/TCC/TCC/ACT/GTT/GC 3' | SEQ ID NO: 36 |
| N1303KN | 5'TCA/TAG/GGA/TCC/AAG/TT 3' | SEQ ID NO: 37 |
| Δ507N | 5'ACA/CCA/AAG/ATG/ATA/Tr 3' | SEQ ID NO: 38 |
| R117HN | 5'CGA/TAG/AGC/GTT/CCT/CC 3' | SEQ ID NO: 39 |
| 621+1N | 5'GCA/AGG/AAG/TAT/TAC/CT 3' | SEQ ID NO: 40 |
| S549NN | See G551 DN sequence | |
| R560TN | 5'TAT/TCA/CCT/TGC/TAA/AG 3' | SEQ ID NO: 41 |
| 1717−1N | 5'GGA/GAT/GTC/CTA/TTA/CC 3' | SEQ ID NO: 42 |
| 3849+10N | 5'ACT/CGC/CAT/TTT/AAT/AC 3' | SEQ ID NO: 43 |
| 3905+TN | 5'GTA/GTC/TCA/AAA/AAG/CT 3' | SEQ ID NO: 44 |
| R347PN | 5'GTG/ACC/GCC/ATG/CGC/AG 3' | SEQ ID NO: 45 |
| 1078dTBN | 5'CAC/CAC/AAA/GAA/CCC[rG 3' | SEQ ID NO: 46 |
| 2789+5GAN | 5'GGA/ATA/CTC/ACT/TTC/CA 3' | SEQ ID NO: 47 |
| 3849+4CN | 5'GCA/GTG/TTC/AAA/TCT/CA 3' | SEQ ID NO: 48 |
| 711+1GTN | 5'CAT/ACT/TCA/TCA/AAT/TT 3' | SEQ ID NO: 49 |
| R1162XN | 5'CTC/GGC/TCA/CAG/ATC/GC 3' | SEQ ID NO: 50 |
| 1898+1GAN | 5'CAT/ACC/TTT/CAA/ATA/TT 3' | SEQ ID NO: 51 |
| 3659dCN | 5'CTT/GGT/AGG/TTT/ACC/TT 3' | SEQ ID NO: 52 |
| G85EN | 5'GAT/TCC/ATA/GAA/CAT/AA 3' | SEQ ID NO: 53 |
| 2184dAN | 5'GAT/TGT/TTT/TTT/GTT/TC 3' | SEQ ID NO: 54 |
| A455EN | 5'AAC/CGC/CAA/CAA/CTG/TC 3' | SEQ ID NO: 55 |
| R334WN | 5'TTC/CGG/AGG/ATG/ATT/CC 3' | SEQ ID NO: 56 |
| Y122XBN | 5'AGA/TAA/ATC/GCG/ATA/GA 3' | SEQ ID NO: 57 |
| S549RBN | 5'TCC/ACT/CAG/TGT/GAT/TC 3' | SEQ ID NO: 58 |
| Q493XN | 5'ACT/GAG/AAC/AGA/ATG/AA 3' | SEQ ID NO: 59 |
| V520FN | 5'GAT/GAC/GCT/TCT/GTA/TC 3' | SEQ ID NO: 60 |
| Y1092XN | 5'ACA/GGT/ACA/AGA/ACC/AG 3' | SEQ ID NO: 61 |
| R347HN | see R347PN sequence | |

Dot Blots

Amplified products were denatured using 1.0N NaOH, 2.0M NaCl, 25 mM EDTA pH 8.0, containing bromophenol blue (30 ml of 0.1% bromophenol blue/10 ml denaturant) for 5 minutes at room temperature. Denatured products were blotted onto Biotrans membrane (ICN Biomedicals Inc., Aurora, Ohio) using a 96-well format dot blot apparatus (Life Technologies, Gaithersburg, Md.). Membranes were neutralized in 2× SSC (0.15M NaCl, 0.015M trisodium citrate) for 5 minutes at room temperature and baked in a vacuum oven at 80° C. for 15 minutes. Immediately before use, the membranes were rinsed in distilled water, and placed in hybridization solution.

Probe Labeling

Aliquots of 106 pooled ASOs (representing each mutation) were thawed, resuspended in distilled water and end-labeled in a single reaction containing 1× kinase buffer (New England Biolabs, Beverly, Mass.), 0.135 nmoles of γ-$P^{32}$-ATP (Dupont, Boston, Mass.) and 35 units of T4 Polynucleotide kinase (New England Biolabs, Beverly, Mass.). The labeling reactions were incubated at 37° C. for 1 hour. The efficiency of the kinase reactions were monitored by chromatography on cellulose polyethyleneimine (PEI) plates (J. T. Baker Inc., Phillipsburg, N.J.) using 0.75M $NaH_2PO_4$ pH 3.5 buffer, followed by exposure of the plates to Kodak X-Omat X-Ray film (Eastman Kodak Company, Rochester, N.Y.) at room temperature for 5 minutes.

Hybridizations

Hybridizations were carried out in plastic bags containing the filters prepared as in Example 1 above, to which pooled radiolabelled ASOs were added in a TMAC hybridization buffer (3.0M TMAC, 0.6% SDS, 1 mM EDTA, 10 mM sodium phosphate pH 6.8, 5× Denhardt's Solution, and 40 μg/ml yeast RNA).

For this protocol, the 96-well array of spotted genomic samples was marked with a grid so that positives identified in the hybridization could be easily located for the subsequent elution and ASO sequencing. Signal intensities generated from the different mutation-positive samples were optimized by adjusting the concentrations of each mutation-specific oligonucleotide within the hybridization. In order to achieve uniform hybridization signals, the final concentration of each labeled mutant ASO in the pool hybridization ranged from 0.008–1.8 pMol/ml, with the concentration of cold normal ASOs ranging from 0–200 fold excess of the corresponding mutant ASO.

Hybridizations were allowed to proceed overnight at 52° C., with agitation. The membranes were then removed from the bags and washed for 20 min at room temperature with wash buffer (3.0M TMAC, 0.6% SDS, 1 mM EDTA, 10 mM sodium phosphate pH 6.8), followed by a second wash in the same buffer for 20 min at 52° C.

Once washed, the blots were wrapped in plastic wrap and exposed to Kodak X-Omat X-Ray film (Eastman Kodak Company, Rochester, N.Y.) at −80° C. for 15 minutes to 1 hour.

EXAMPLE 3

Separation of Hybridized ASOs

Pool-positive samples from hybridizations performed as in Example 2 are treated as follows: Positive spots are excised in the form of discs from the nylon membrane using a standard single hole paper punch. Each of the excised membrane discs is then placed in separate 0.315 ml microcentrifuge tubes containing 100 μl of sterile water, and the tubes are incubated at 100° C. for 15 minutes (FIG. 4.)

EXAMPLE 4

Design of Complementary Oligonucleotides for Identification of Bound ASOs

The sequence of the polymers may be determined directly using chemical sequencing. Alternatively, polymers may be used in conjunction with complementary oligonucleotides that contain other sequences in addition to sequences complementary to the polymers. In these cases, the polymers serve as primers to form extension products that contain the additional sequences, and the extension products are subjected to DNA sequencing.

Specific Mutation Identification

A. By chemical cleavage

The ASO hybridized to each mutation-positive sample was identified by eluting and sequencing the ASO. For the pool of 106 ASOs, sequencing "C" and "G" bases only was sufficient to unambiguously identify the ASO sequence and therefore allowed unequivocal identification of the corresponding mutation in the DNA sample.

The region of membrane containing each mutation-positive sample identified in the pool hybridization was excised and the disc of Biotrans membrane placed in 100 ml distilled water and heated at 95° C. for 10 minutes to elute the bound ASO. After cooling to room temperature, the membrane disc was discarded, and the eluted ASO was subjected to chemical sequencing.

Solid-phase chemical cleavage of the ASOs attached to a solid support was performed according to Rosenthal et al. (32) with minor changes. This method permitted simultaneous sequencing of all bound ASOs in a single reaction vessel. To attach the ASOs to a solid support prior to chemical cleavage, a small, labeled piece (6 mm×3 mm) of CCS paper (32) was immersed in each tube containing eluted ASO, and incubated at 65° C. for 1 hour. All pieces of paper were then combined into a single 50 ml tube containing 25 ml of distilled water. The papers were then washed at room temperature 3 times (30 sec./wash) with distilled water (25 ml/wash) followed by 3 washes (30 sec./wash) with 96% ethanol (25 ml/wash). Papers with attached ASOs could be batch washed without cross-contamination.

Once washed, the papers were air-dried and each piece cut into two, with ⅓ assigned for the "G" chemical cleavage reaction and ⅔ designated for the "C" cleavage reaction. All "C" reaction ASO-solid supports were combined into one tube containing 1 ml 4.0M hydroxylamine HCl pH 6. For "G" reaction modifications, the combined pieces of paper were placed in 1 ml 50 mM ammonium formate pH 3.5 and 7 ml of DMS added. Reactions were incubated at room temperature for 10 minutes or 20 minutes for the "G" and "C" reaction respectively. Batch processing of over 100 sequencing reactions was performed without cross-contamination of cleavage products.

Washes were performed on the batch of "C" reaction papers and the batch of "G" reaction papers as described above for washes after attachment of the ASOs to the solid support. The papers were then air dried and each piece of paper placed in their designated location in a 96-well amplification tray (Perkin-Elmer, Norwalk, Conn.)

To cleave and elute the sequencing products off the solid support membrane, freshly prepared piperidine (50 µl of 10% (v/v) piperidine) was added to each well, the tray was covered with a rubber gasket, and incubated at 90° C. for 30 minutes in a thermal cycler.

For each cleavage reaction, the piperidine solution containing the eluted cleavage products was transferred to a fresh 96-well amplification tray and the piperidine evaporated. The evaporation step was repeated twice with 50% ethanol (35 µl/well). ASO cleavage products were dissolved in 4 ml loading dye (90% formamide, 1× TBE, 0.1% bromophenol blue, 0.1% xylene cyanol) before gel electrophoretic resolution. Sequencing gels (20% polyacrylamide/ 8M urea/TBE) were pre-run for 1 hour at 2000 V, the samples were loaded, and electrophoresis continued until the bromophenol blue dye had migrated 14 cm from the origin. Sequencing gels were exposed to Kodak X-Omat X-ray film for 24–48 hours.

B. By enzymatic sequencing

Mutation-positive samples were identified, spots excised and ASOs eluted as described for the chemical cleavage method. The eluted samples were each placed in Microcon-10™ concentrators (Amicon Inc., Beverly, Mass.) and centrifuged at 14,000 rpm for 15 minutes in a bench top microfuge. The eluates were then tansferred to Microcon-3™ concentrators (Amicon Inc., Beverly, Mass.) and centrifuged at 14,000 rpm for 30 minutes in a bench top microfuge. Both concentrators were washed twice with 100 µl distilled water per wash. (The Microcon-3™ concentrators were washed with the eluate from the corresponding Microcon-10™ concentrators). The eluted ASOs were recovered from the top portion of the Microcon-3™ concentrator by 3 serial rinses with 20 µl distilled water/rinse, and the fractions pooled. The samples were lyophilized in a UniVapo™ concentrator (Integrated Separation Systems, Natick, Mass.), re-dissolved in 5 µl of distilled water, and used as sequencing primers in an enzymatic sequencing protocol designed to identify the eluted ASO. The sequencing reactions included a pool of oligonucleotide templates with each template (77-mer) consisting of a 3' region (17 bp) as the primer binding site uniquely complementary to a specific ASO, and a second unique region (17 bp) consisting of an "ASO-specific identifier sequence". Sequencing products were only observed when an eluted ASO was bound to the complementary region of a unique template, acted as a primer and permitted cycle sequencing to reveal the identity of the downstream "ASO-specific identifier sequence".

The cycle sequencing reactions contained a pool of ASO-specific templates (5 fmoles/template), 0.5 µl of Thermosequenase buffer concentrate (Amersham Life Science, Cleveland, Ohio), 0.125 µl of Thermosequenase (32 U/µl), and either 'G' termination mix (15 mM dATP, 15 mM dCTP, 15 mM dTTP, 15 mM 7-deaza-dGTP and 4 mM ddGTP) or 'C' termination mix (15 mM dATP, 15 mM dGTP, 15 mM dTTP, 15 mM 7-deaza-dGTP and 4 mM ddCTP) in a reaction volume of 8 µl. Cycle sequencing was performed between 95° C. for 30 seconds and 70° C. for 1 minute for 30 cycles, followed by a 2 minute incubation at 70° C. Sequencing products were resolved on a 15% acrylamide/ 7M urea gel before being exposed to Kodak X-Omat X-ray film at −70° C. for about 16 hours.

The following are examples of several complementary oligonucleotides that contain the complement of the R334W CF mutation-specific ASO identified hereinabove.

Version 1

ASO as sequencing primer

---

SEQ ID NO: 62
3'-AAGGTCTCCTACTAAGG-TCTCGCTTCGTTTCATCTCATCTCG-5'
    ASO complement       "Tag"

---

In this embodiment, an ASO is incubated with the complementary oligonucleotide in a Sanger sequencing reaction, and the sequence is determined directly.

Version 2

Cycle sequencing of eluted ASO

---

3'-AAGGTCTCCTACTAAGG-TCTCGCTTCGTTTCATCTCATCTCT-
    ASO complement       "Tag"
ATCGATCGATCGATCGATCGATCG-5' SEQ ID NO: 63
    Universal Primer Sequences

---

In this embodiment, an ASO serves as a primer for a single extension reaction. The extension product is then subjected to cycle sequencing, using the universal primer to prime the sequencing reaction (see Example 5 below.).
Version 3
Amplification of complementary oligonucleotide for Sanger sequencing

EXAMPLE 6

Amplification and Sequencing of Complementary oligonucleotides

A separated mutation-specific oligonucleotide, designated R334W and having the sequence

---

3'-AAGGTCTCCTACTAAGG-CGCCAGGGTTTTCCCAGTCA-
    ASO complement    "sequencing target"
TCTCGCTTCGTTCATCTCATCTCG-ATCGATCGATCGATCGATCGA-5'
    "Tag"    Universal Primer Sequence
SEQ ID NO: 64

---

In this embodiment, an ASO serves as a primer for a single extension reaction. The extension product is then amplified using the universal primer sequence and the ASO as amplification primers. Finally, the amplification products are subjected to Sanger sequencing using as a primer an oligonucleotide corresponding to the sequencing target (see Example 6 below.).

EXAMPLE 5

Cycle Sequencing of ASOs
A) Extension Reaction

A separated mutation-specific oligonucleotide, designated R334W and having the sequence 5'-TTCCAGAGGATGATTCC-3' SEQ ID NO:65 is added to a reaction mix containing reaction components necessary for a single round of extension. The complementary oligonucleotide (Version 2 in Example 4 above) contains a universal primer sequence at its 5' end, separated by 25–30 bases from the complement to R334W at its 3' end. The extension reaction contains the following components:

25 µl separated ASO
5 µl 10× buffer (0.5 mM Tris-HCl pH 7.5, 0.1M MgCl$_2$, 10 mM dithiothreitol)
1 µl dNTPs (2.5 mM each)
    1 µl complementary oligonucleotides (100 ng/ml)
    13 µl H$_2$O
1 µl Klenow fragment of DNA polymerase (10 U/µl)

The reaction is allowed to proceed at room temperature for 30 minutes.

B) Cycle Sequencing

An aliquot of the above reaction is added to a PCR reaction mix containing two or more dideoxynucleotide analogues (ddNTPs), according to the following protocol:

10 µl extension products
5 µl 10× buffer (300 mM Tris-HCl pH 9.0, 50 mM MgCl$_2$, 300 mM KCl)
5 µl universal primer (1 pmole)
10 µl 2mM ddATP, ddCTP, ddGTP; 100 µM dATP, dCTP, dGTP, dTTP
19 µl H$_2$O
1 µl Taq polymerase (10 U/µl)

30 cycles of amplification are performed, creating a heterogeneous population of random termination products that terminate at positions corresponding to nucleotides downstream of the universal primer sequence. The products of the PCR reaction are then separated in a denaturing polyacrylamide gel, creating a banding pattern specific for this ASO. The electrophoretic pattern is analyzed by autoradiography or fluorimetry.

5'-TTCCAGAGGATGATTCC-3' is added to a reaction mix containing reaction components for extension as in Example 5, Step A. The complementary oligonucleotide (Version 3 in Example 4 above) contains a universal primer sequence at its 5' end, a "tag" sequence, "sequencing target" sequence, followed by the complement to R334W at its 3' end. Following the extension reaction, an aliquot of the reaction is added to an amplification mixture containing the following components:

3 µl extension products
1 µl universal amplification primer (10 µM)
2.5 µl dATP, dTTP, dCTP, dGTP (2 mM each)
2 µl 40 mM MgCl$_2$
5 µl 100 mM Tris-HCl pH 8.3, 500 mM KCl
26.4 µl H$_2$O
0.1 µl Amphitaq DNA polymerase (5 U/µl).

The reaction is then subjected to 35 cycles of amplification, using a GeneAmp PCR System 9600 Thermocycler. 2 µl of the amplification products are then removed and subjected to Sanger sequencing, using the Sanger sequencing primer.

EXAMPLE 7

RNA as a Target Nucleic Acid

In a similar manner to Example 1, which describes DNA as a target nucleic acid, RNA may also be used as a target nucleic acid.

A) Preparation of RNA from Target Cells

Cells are collected by centrifugation, and the supernatant is removed. The cell pellet is suspended in cold lysis buffer (140 mM NaCl, 1.5 mM MgCl$_2$, 1.0 mM Tris-Cl, pH 8.5, 0.5% NP-40, and Rnasin® (Promega, Inc.)). Cellular debris is pelleted by centrifugation for 5 minutes at 4° C. at 5000×g. The supernatant is transferred to a fresh tube and the EDTA concentration brought to 10 mM. Proteins are removed by extraction with phenol-chloroform saturated with aqueous 10 mM Tris, pH 8.5. The aqueous phase is precipitated with sodium acetate at pH 5.2 and 2.5 volumes of ice cold ethanol overnight at 10° C. RNA is collected by centrifugation at 10,000×g at 4° C. for 30 minutes.

B) Conversion of RNA to cDNA Before Amplification

RNA may be used directly in the manner of the present invention, or converted to amplified DNA via a reverse transcription PCR protocol. According to this protocol, 1 µg of RNA is mixed with 100 pmol of appropriate primers, 1 mM dNTPs, 1 U/µl RNasin® in 20 µl PCR buffer (50 mM KCl, 20 mM Tris, pH 8.4, 2.5 mM MgCl$_2$) and 200 U of reverse transcriptase. The mixture is incubated at 23° C. for 10 minutes, then 42° C. for 45 minutes, then 95° C. for 5 minutes, and then quick chilled. Conventional PCR Protocols, similar to hose described in Example 1, may be used Go amplify the resultant cDNA.

EXAMPLE 8

Unique Probe Identifiers

Instead of determining the identity of the separated polymer using chemical or enzymatic sequencing reactions, it is also possible to label each probe polymer with a unique identifier moiety that can be detected directly or indirectly. The following description merely demonstrates examples of the full range of unique probe identifiers that one of skill would readily understand to have use in the present invention.

A) Fluorescent Labels

Oligonucleotides are hybridized to immobilized nucleic acid targets in a similar manner as described in Example 2 above, except that each ASO in the pool is labeled with a unique fluorescent probe instead of $^{32}P$ For example, ASOs designated ΔF508M, G542XM, G55IDM and R553XM are labeled with Texas Red, tetramethylrhodamine, fluorescein, and Cy3, respectively. Similar to Example 3, bound ASOs can be detected as having been bound prior to separation. In this Example, ASO binding is detected by any number of automated methods. After separation, the ASO can be positively identified by measuring emission wavelength in response to fluor excitation.

B) Molecular Weight Labels

Oligonucleotides are hybridized to immobilized nucleic acid targets in a similar manner as described in Example 2 above, except that each ASO in the pool is additionally labeled with a unique molecular weight modifying entity. For example, the four ASOs described in Example 8A are each derivatized with a 5' oligomeric hexaethyleneoxide (HEO) tail of differing length. ASOs designated ΔF508M, G542XM, G551DM and R553XM can be labeled with lengths of 5, 10, 15 and 20 HEO units, respectively. The tails are added using standard DNA synthesis protocols such as those described in Nucleic Acid Res, 22:4527. The HEO tail does not participate in hydrogen bonding but does give a unique molecular weight to each ASO. The ASO can be identified without further modification by distinguishing the separated ASOs by molecular weight, using any number of commonly recognized methods, such as gel or capillary electrophoresis.

C) Alternative Molecular Weight Labeling Method

An additional method of utilizing molecular weight identification of the hybridizing polymer is to add an additional number of nucleotides to the polymer enzymatically after separation from target nucleic acid. In a preferred embodiment of this method, the separated polymer, after hybridization to the immobilized nucleic acid target, is collected into a tube containing oligonucleotides, each of which is complementary to one member of the polymer pool used to probe the target nucleic acid. In addition to a portion that is complementary to the polymer, the oligonucleotide also contains an additional sequence, the length of which is unique for that oligonucleotide. When the polymer and oligonucleotide hybridize, the polymer can subsequently be used as a primer to enzymatically extend the polymer co the full length of the complementary oligonucleotide. During this process, a direct or indirect label, as described above, may be incorporated. The extended oligonucleotide can be identified by determining the relative molecular weight of the labeled product by any number of established methods, such as gel or capillary electrophoresis.

EXAMPLE 9

Ligation of Polymers

Figure 5:
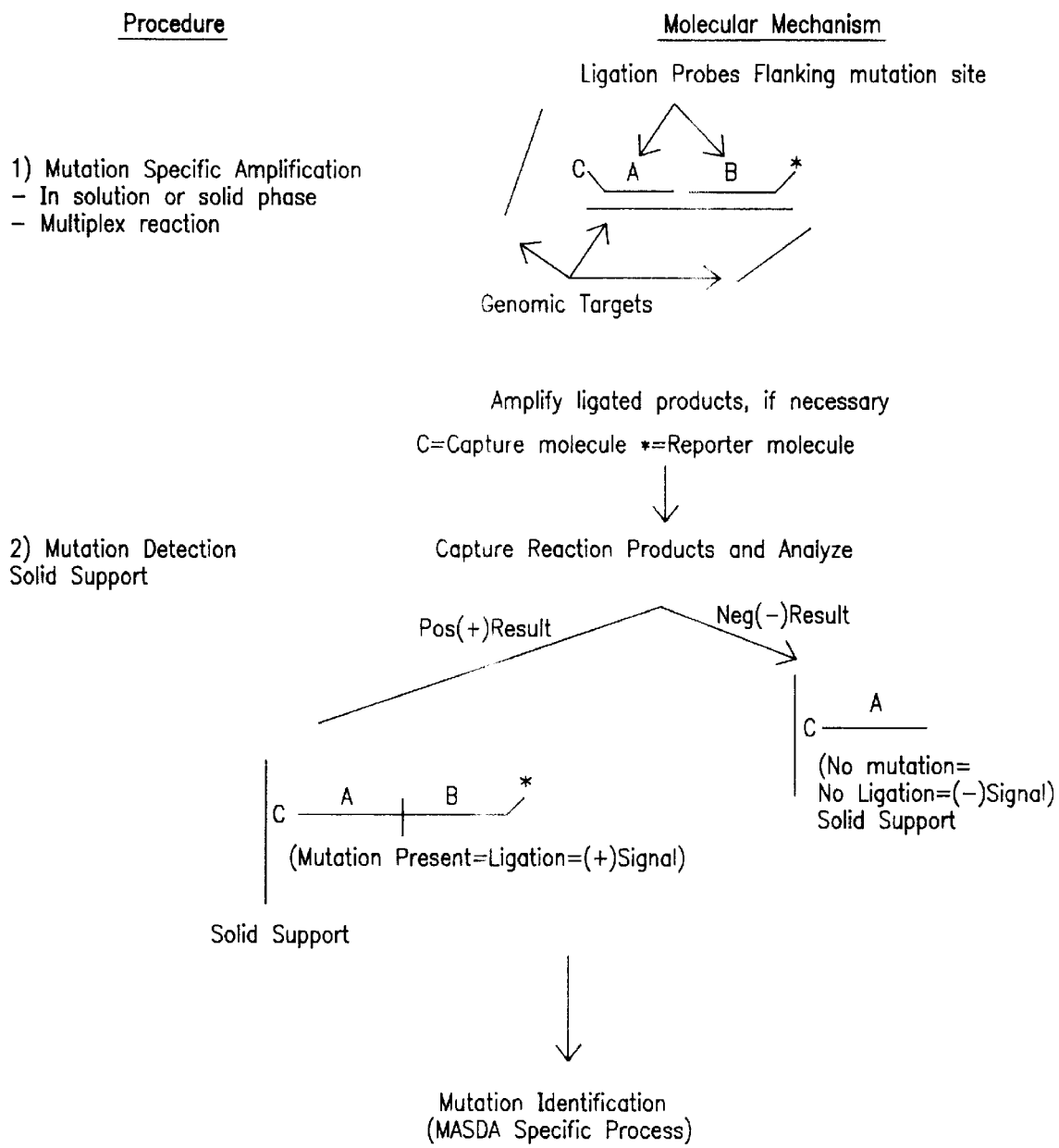
FIG. 5 depicts general schemes for ligation based techniques for hybridizing purine and pyrimidine polymers to immobilized samples and identifying the hybridized products.

Ligation based techniques are known for identifying polymers probes that have perfectly hybridized to a sample. Ligation is often used in such techniques to distinguish perfect from imperfect hybridization at the junction of adjacent polymer probes. This is particularly useful for determining genetic alterations. (Landegren et al., 1988, Science 241:1078). LCR is one technique that results in amplification of the ligated products and can be used to aid in obtaining sufficient copies of the product to determine the presence of the target sequence. Gap-LCR is a modification of LCR that reduces the background generated by target-independent ligation. Other ligation related amplification techniques are listed above. FIG. 5 schematically depicts some examples of ligation techniques that can be used in the present invention. In these schemes polymers form ligation probes that, e.g., flank the site of a genetic alteration. One of the polymers (or probes) of each pair has a capture molecule attached. The other has a reporter molecule attached. After the polymers are hybridized to immobilized samples, and ligated, any non-hybridized polymers may be washed away. Washing away of unhybridized polymers is not always necessary, although it is strongly preferred, particularly where a large number of polymers is reacted with the samples (an excess of unhybridized polymers can interfere with identification of ligated polymers by e.g. sequencing). Nor does the sample need to be immobilized since it is possible to carry out hybridization and ligation of the probes in solution. Furthermore, imperfect hybrids can form under conditions used in ligation procedures. TMAC and strict temperature control are often not required. Imperfect hybrids, however, do not register as false positives because they do not ligate, and therefore are not identified.

The ligated products can then be amplified to allow easier identification. For example, LCR thermocycling accomplishes this. Alternately, it is possible to amplify the ligated products using other techniques, such as PCR. It is also possible to amplify the amount of sample DNA prior to the hybridization step so that, if a sufficient quantity of polymer probes is used, the ligated products will not need to be amplified.

The hybridized and ligated polymers are then captured on a solid support. The presence of the reporter molecule is then determined. If the reporter is present, then ligation has occurred, and the presence of the target molecule determined.

Various schemes to identify the target sequence that the ligated polymers are specific for will be apparent to one skilled in the art. Four such schemes are depicted in FIGS. 6–9, indicated as "Models" 1–4. In Model 1 (FIG. 6), genetic alterations, target nucleic acid sequences, or randomly permuted alterations that resulted in ligation of the polymers are identified through chemical cleavage sequencing of the products, i.e., Maxam-Gilbert type sequencing. In Model 2 FIG. 7), the ligation products are sequenced in a conventional Sanger type sequencing reaction. Specifically, after the ligation products are captured on a solid phase, a heterogeneous population of sequences is added that includes a sequence that hybridizes to the ligation product. Sequencing is carried out, and the ligation product identified. In Model 3, (FIG. 8) ligation products are directly sequenced by conventional Sanger sequencing using heterogeneous primers that are complementary to sequences in the "B" portion of the ligation product depicted. Alternately, sequencing is done using a primer complementary to a common 3' tether added to the "B" probes. In Model 4 (FIG. 9), the ligation product is used as a template for a linear amplification using a universal priming sequence. The reaction can be performed with the product either attached to a solid phase or in solution. The products are conventionally

EXAMPLE 10

ARMS Amplification of Polymers

The amplification refractory mutation system is a known PCR type system for determining mutations and can be used to practice the present invention. For example, polymers are synthesized that are complementary to a sequence that may contain a mutation, and that act as primers when hybridized to the target DNA. Primers that are complementary to wild type sequence(s) are unlabelled. Primers that are complementary to a mutant sequence(s) are Labelled. A second polymer is synthesized that is designed to act as a primer allowing PCR amplification when used in combination with the first set of primers. The second polymer is attached to one member of a binding pair, e.g., biotin, that allows capture of amplified PCR products on a solid phase. The polymer/primers are hybridized to the sample, and PCR thermocycling is then carried out. The amplified products are then exposed to a solid phase having a binding partner (e.g. avidin) attached to its surface. Presence of a signal on the amplified products bound to the support surface indicates that a mutant sequence was present in the sample. The bound products can then be identified using methods described above, e.g. Sanger sequencing.

Invention methodologies provided herein retain the capacity for large sample throughput while reducing the number of hybridizations involved in performing multiple mutation analysis. If the number of probes for any diagnostic test is extremely large, the large number of independent hybridizations to be Performed on pool positive samples reduces the cost effectiveness of the invention methodology. Using the MASDA approach of the instant invention, the disadvantages of both individual sample hybridizations and independent probe hybridizations are avoided. By eluting and interrogating the sequence of the mutation-specific oligonucleotides hybridized to a DNA sample, MASDA eliminates the need for secondary independent hybridizations. Therefore, in a single day, hundreds of different samples can be simultaneously analyzed in a single hybridization containing a complex mixture of hundreds of mutation-specific oligonucleotides. Also, by generating short and unique band patterns for the hybridized and eluted oligonucleotides, multiple samples can be analyzed by stagger loading samples across multiple lanes of a gel. Therefore, using currently available automated sequencers, specific mutation identification can easily be performed on hundreds of pool positive samples at a rake in excess of 150 samples/hour.

In addition to high throughput sample capacity and complex mutation analysis, there are several other advantages to the invention MASDA technology. MASDA is an extremely flexible, modular platform. This is very important in a field such as genetic diagnostics, where the number of relevant genes, and mutations identified in each gene, change rapidly. Having oligonucleotide probes in solution, it is possible to mix and match probes on demand, therefore allowing clinical laboratories to cost-effectively customize diagnostic assays. There is also flexibility in sample preparation, and target detection. The sample nucleic acid can be either DNA or RNA.

For exemplification of multiple target amplifications, PCR was utilized as the amplification procedure. However, the present invention, MASDA, is compatible with any amplification technology, and does not require any processing of amplification products prior to mutation detection and identification. This becomes a very important issue when large numbers of samples need to be analyzed in a single assay. Since the sample nucleic acid does not need to be fragmented, long PCR products can be analyzed, as well as the multiplex amplicons demonstrated in this study.

Currently, significant efforts are being established to develop informative databases on genotype/phenotype associations of existing and new mutations within known disease genes. Additionally, there is an ever increasing interest in establishing the relationships between genotypes of patients involved in clinical trials and their response to various therapeutic treatments. The present invention MASDA will facilitate the development of oligonucleotide libraries representative of previously identified expressed sequence tags or bi-allelic markers identified within the human genome.

REFERENCES

1. Wilson, J. T., Marotta, C. A., Forget, B. G. and Weissman, S. M. (1977) Structure of hemoglobin messenger RNA and its relation to hemoglobinopathies. Trans. Assoc. Am. Physicians 90, 117–126.
2. Fearon, E. R. and Vogelstein, B. (1990) A genetic model for colorectal tumorigenesis. Cell, 61, 759–767.
3. Miki, Y., Swenson, J., Shattuck-Eidens, D., Futreal, P. A., Harshman, K., Tavtigian, S., Liu, Q., Cochran, C., Bennett, L. M., Ding, W., Bell, R., Rosenthal, J., Hussey, C., Tran, T., McClure, M., Frye, C., Hattier, T., Phelps, R., Haugen-Strano, A., Katcher, H., Yakumo, K., Gholami, Z., Shaffer, D., Stone, S., Bayer, S., Wray, C., Bogden, R., Dayananth, P., Ward, J., Tonin, P., Narod, S., Bristow, P. K., Norris, F. H., Helvering, L., Morrison, P., Rosteck, P., Lai, M., Barrett, J. C., Lewis, C., Neuhausen, S., Cannon-Albright, L., Goldgar, D., Wiseman, R., Kamb, A. and Skolnick, M. H. (1994) Isolation of a strong candidate for the 17q-linked breast and ovarian cancer susceptibility gene, BRCA1. Science, 266, 66–71.
4. Wooster, R., Bignell, G., Lancaster, J., Swift, S., Seal, S., Mangion, J., Collins, N., Gregory, S., Gumbs, C., Micklem, G., Barfoot, R., Hamoudi, R., Patel, S., Rice, C., Biggs, P., Hashim, Y., Smith, A., Connor, F., Arason, A., Gudmundsson, J., Ficenec, D., Kelsell, D., Ford, D., Tonin, P., Bishop, D. T., Spurr, N. K., Ponder, B. A. J., Eeles, R., Peto, J., Devilee, P., Cornelisse, C., Lynch, H., Narod, S., Lenoir, G., Egilsson, V., Barkadottir, R. B., Easton, D. F., Bentley, D. R., Futreal, P. A., Ashworth, A. and Stratton, M. R. (1995) Identification of the breast cancer susceptibility gene, BRCA2. Nature, 378, 789–792.
5. Cotton, R. G. H. (1993) Current methods of mutation detection. Mutat Res, 285, 125–144.
6. Forrest, S., Cotton, R., Landegren, U. and Southern, E. (1995) How to find all those mutations. Nat Genet, 10, 375–376.
7. Orita, M., Iwahana, H., Kanazawa, H., Hayashi, K. and Sekiya, T. (1989) Detection of polymorphisms of human DNA by gel electrophoresis as single-strand conformation polymorphisms. Proc Natl Acad Sci U.S.A., 86, 2766–2770.
8. Myers, R. M., Lumelsky, N., Lerman, L. S. and Maniatis, T. (1985) Detection of single base substitutions in total genomic DNA. Nature, 313, 495–498.
9. Keen, J., Lester, D., Inglehearn, C., Curtis, A. and Bhattacharya, S. (1991) Rapid detection of single base mismatches as heteroduplexes on Hydrolink gels. Trends Genet, 7, 5.
10. Cotton, R. G. H., Rodrigues, N. R. and Campbell, R. D. (1988) Reactivity of cytosine and thymine in single-basepair mismatches with hydroxylamine and osmium tetroxide and its application to the study of mutations. Proc Natl Acad Sci U.S.A., 85, 4397–4401.
11. Myers, R. M., Larin, Z. and Maniatis, T. (1985) Detection of single base substitutions by ribonuclease cleavage at mismatches in RNA:DNA duplexes. Science, 230, 1242–1246.
12. Sanger, F., Nicklen, S. and Coulson, A. R. (1977) DNA sequencing with chain-terminating inhibitors. Proc Natl Acad Sci U.S.A., 74, 5463–5467.
13. Newton, C. R., Graham, A., Heptinstall, L. E., Powell, S. J., Summers, C., Kalsheker, N., Smith, J. C. and Markham, A. F. (1989) Analysis of any point mutation in DNA. The amplification refractory mutation system (ARMS). Nucl Acids Res, 17, 2503–2516.
14. Landegren, U., Kaiser, R., Sanders, J. and Hood, L. (1988) A ligase-mediated gene detection technique. Science, 241, 1077–1080.
15. Sokolov, B. P. (1990) Primer extension technique for the detection of single nucleotide in genomic DNA. Nucl Acids Res, 18, 3671.
16. Cohen, J. B. and Levinson, A. D. (1988) A point mutation in the last intron responsible for increased expression and transforming activity of the c-Ha-ras oncogene. Nature, 334, 119–124.
17. Wallace, B. R., Johnson, M. J., Hirose, T., Miyake, T., Kawashima, E. H. and Itakura, K. (1981) The use of synthetic oligonucleotides as hybridization probes. II. Hybridization of oligonucleotides of mixed sequence to rabbit b-globin DNA. Nucl Acids Res, 9, 879–894.
18. Saiki, R. K., Walsh, P. S., Levenson, C. H. and Erelich, H. A. (1989) Genetic analysis of amplified DNA with immobilized sequence-specific oligonucleotide probes. Proc Natl Acad Sci U.S.A., 86, 6230–6234.
19. Drmanac, R., Labat, I., Brukner, I. and Crkvenjakov, R. (1989) Sequencing of megabase plus DNA by hybridization: theory of the method. Genomics, 4, 114–128.
20. Bains, W. and Smith, G. C. (1988) A novel method for nucleic acid sequence determination. J Theor Biol, 135, 303–307.
21. Khrapko, K. R., Lysov, Y., Khorlyn, A. A., Shick, V. V., Florentiev, V. L. and Mirzabekov, A. D. (1989) An oligonucleotide hybridization approach to DNA sequencing. FEBS Lett, 256, 118–122.
22. Southern, E. M., Maskos, U. and Elder, J. K. (1992) Analyzing and comparing nucleic acid sequences by hybridization to arrays of loigonucleotides: evaluation using experimental models. Genomics 13, 1008–1017.
23. Pease, A. C., Solas, D., Sullivan, E. J., Cronin, M. T., Holmes, C. P. and Fodor, S. P. A. (1994) Light-generated oligonucleotide arrays for rapid DNA sequence analysis. Proc Natl Acad Sci U.S.A., 91, 5022–5026.
24. Guo, Z., Guilfoyle, R. A., Theil, A. J., Wang, R. and Smith, L. M. (1994) Direct flourescence analysis of genetic polymorphisms by hybridization with oligonucleotide arrays on glass supports. Nucl Acids Res, 22, 5456–5465.
25. Shuber, A. P., Skoletsky, J., Stern, R. and Handelin, B. L. (1993) Efficient 12-mutation testing in the CFTR gene: A general model for complex mutation analysis. Hum Mol Gen, 2, 153–158.
26. Zielenski, J., Rozmahel, R., Bozon, D., Kerem, B. S., Grzelczak, Z., Riordan, J. R., Rommens, J. and Tsui, L. C. (1991) Genomic DNA sequence of the cystic fibrosis transsmemorane conductance regulator (CFTR) gene. Genomics, 10, 214–228.
27. Myerowitz, R. and Costigan, F. C. (1988) The major defect in Askenazi Jews with Tay-Sachs disease is an insertion in the gene for the alpha-chain of beta-hexosaminidase. J Biol Chem, 263, 18587–18589.
28. Horowitz, M., Wilder, S., Herowitz, Z., Reiner, O., Gelbart, T. and Beutler, E. (1989) The human glucocerebrosidase gene and pseudogene: structure and evolution. Genomics, 4, 87–96.
29. Kaul, R., Gao, G. P., Balamurugan, K. and Matalon, R. (1993) Cloning of the human aspartoacylase cDNA and a common missense mutation in Canavan disease. Nat Gen, 5, 118–123.
30. Whitney, M. A., Saito, H., Jakobs, P. M., Gibson R. A., Moses, R. E. and Grompe, M. (1993) A common mutation in the FACC gene causes Fanconi Anemia in Askenazi Jews. Nat Gen, 4, 202–205.
31. Wood, W. I., Gizschier, J., Lasky, L. A. and Lawn, R. M. (1985) Base composition-independent hybridization in tetramethylammonium chloride: A method for oligonucleocide screening of highly complex gene libraries. Proc. Natl. Acad. Sci. U.S.A. 82, 1585–1588.
32. Rosenthal, A., Schwertner, S., Hahn, V. and Hunger, H. D. (1985) Solid-phase methods for sequencing of nucleic acids I. Simultaneous sequencing of different oligodeoxyribonucleotides using a new, mechanically stable anion-exchange paper. Nucl Acids Res, 13, 1173–1184.
33. Shuber, A. P., Grondin, V. J. and Klinger, K. W. (1995) A simplified procedure for developing multiplex PCRs. Genome Research 5, 488–493.

What is claimed is:

1. A method for identifying one or more genetic alterations in a target sequence present in a nucleic acid sample, comprising the steps of:

(i) immobilizing a plurality of nucleic acid samples on a support;

(ii) contacting said immobilizes samples simultaneously with a multiplicity of different purine and pyrimidine containing polymers under conditions wherein individual purine and pyrimidine containing polymers hybridize to a complementary target sequence in said immobilized samples;

(iii) separating the hybridized purine and pyrimidine containing polymers from said immobilized samples; and (iv) identifying the hybridized purine and pyrimidine containing polymers,
wherein the identification of the hybridized purine and pyrimidine containing polymers identifies said genetic alteration(s).

2. A method for identifying one or more target sequences present in a nucleic acid sample, comprising the steps of:

(i) immobilizing a plurality of nucleic acid samples on a support;

(ii) contacting said immobilized samples simultaneously with a multiplicity of different purine and pyrimidine containing polymers under conditions wherein individual purine and pyrimidine containing polymers hybridize to a complementary target sequence in said immobilized samples;

(iii) separating the hybridized purine and pyrimidine containing polymers from said complementary target sequence(s); and (iv) identifying the hybridized purine and pyrimidine containing polymers,
wherein the identification of the hybridized purine and pyrimidine containing polymers identifies said target sequence(s).

3. The method of claim 2, wherein the nucleic acid sample is suspected of containing more than one target sequences.

4. The method of claim 2, wherein the target sequence is selected from the group consisting of viral, bacterial, fungal, and protozoal nucleic acid sequences.

5. A method for identifying one or more randomly permuted genetic alterations in a target sequence present in a nucleic acid sample, comprising the steps of:

(i) immobilizing a plurality of nucleic acid samples on a support;

(ii) contacting said immobilized samples simultaneously with a multiplicity of different purine and pyrimidine containing polymers under conditions wherein individual purine and pyrimidine containing polymers hybridize to a complementary target sequence in said immobilized samples;

(iii) detecting hybridization between said purine and pyrimidine containing polymers and said complementary target sequences,
wherein the detection of the hybridized purine and pyrimidine containing polymers identifies said target sequence(s);

(iv) separating said hybridized purine and pyrimidine containing polymers from said complementary target sequences; and (v) identifying one or more randomly permuted genetic alterations present in said target sequence.

6. The method of claim 1, wherein said genetic alterations comprise nucleotide insertions, deletions, or substitutions.

7. The method of claim 1, wherein the nucleic acid samples are suspected of containing one or more genetic alterations.

8. The method of claim 7, wherein the genetic alteration is associated with a disease selected from the group consisting of cystic fibrosis, β-thalassemia, Tay-Sachs disease, sickle cell anemia, and Gaucher's disease.

9. The method of claim 1, wherein said purine and pyrimidine containing polymers are from 16 to 25 bp in length.

10. The method of claim 1, wherein the target sequence is amplified from the nucleic acid samples prior to the immobilizing step.

11. The method of claim 1, wherein the amplified sequence is from 80 bp to about 30 kbp in length.

12. The method of claim 1, wherein said purine and pyrimidine containing polymers are of approximately the same length and said contacting step occurs in the presence of an effective concentration of an agent that eliminates disparities in the melting temperatures of hybrids formed between said purine and pyrimidine containing polymers and said target sequence(s).

13. The method of claim 12, wherein the agent is a quaternary ammonium salt.

14. The method of claim 1, wherein the identifying step comprises:

(a) contacting said hybridized purine and pyrimidine containing polymers with a multiplicity of complementary oligonucleotides comprising (i) sequences complementary to said polymers and (ii) additional predetermined colinear sequences;

(b) performing enzymatic sequencing, wherein said polymers serve as primers and the complementary oligonucleotides serve as templates for enzymatic sequencing; and (c) identifying the predetermined colinear sequences as an indicator of the presence of said polymers.

15. The method of claim 1, wherein the identifying step comprises:

(a) contacting said hybridized purine and pyrimidine containing polymers with a multiplicity of complementary oligonucleotides comprising (i) sequences complementary to said polymers and (ii) additional predetermined colinear sequences;

(b) performing a single extension reaction, wherein said polymers serve as primers and the complementary oligonucleotides serve as templates for the extension reaction;

(c) performing enzymatic sequencing of the products of the extension reaction; and (d) identifying the predetermined colinear sequences as an indicator of the presence of said polymers.

16. The method of claim 1, wherein said purine and pyrimidine polymers are each provided with a molecular weight modifying entity having a unique molecular weight.

17. The method of claim 1, wherein said purine and pyrimidine polymers are provided with a detectable label.

18. The method of claim 1 wherein the purine and pyrimidine containing polymers that do not hybridize to said immobilized samples are removed prior to said identifying step.

* * * * *